United States Patent
Kaneko et al.

(10) Patent No.: US 8,803,101 B2
(45) Date of Patent: Aug. 12, 2014

(54) RADIOLOGICAL IMAGE DETECTION APPARATUS AND RADIATION IMAGING APPARATUS

(71) Applicant: FUJIFILM Corporation, Tokyo (JP)

(72) Inventors: Yasuhisa Kaneko, Kanagawa (JP); Haruyasu Nakatsugawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/972,009

(22) Filed: Aug. 21, 2013

(65) Prior Publication Data
US 2013/0334427 A1    Dec. 19, 2013

Related U.S. Application Data

(63) Continuation of application No. PCT/JP2012/053970, filed on Feb. 20, 2012.

(30) Foreign Application Priority Data

Feb. 21, 2011    (JP) ................................ 2011-035227

(51) Int. Cl.
*G01T 1/20*    (2006.01)
*H01L 27/146*    (2006.01)

(52) U.S. Cl.
USPC ................................ 250/370.11; 250/370.09

(58) Field of Classification Search
USPC ............................ 250/361 R, 370.09, 370.11
See application file for complete search history.

(56) References Cited

U.S. PATENT DOCUMENTS

| | | | |
|---|---|---|---|
| 2004/0016886 A1 | 1/2004 | Ringermacher et al. | |
| 2004/0042585 A1* | 3/2004 | Nagarkar et al. | 378/98.8 |
| 2010/0193691 A1 | 8/2010 | Ishii et al. | |
| 2011/0006213 A1 | 1/2011 | Sato et al. | |
| 2011/0017912 A1* | 1/2011 | Goto et al. | 250/361 R |
| 2011/0272737 A1 | 11/2011 | Tanaka et al. | |

FOREIGN PATENT DOCUMENTS

| JP | 2001095789 A | 4/2001 |
|---|---|---|
| JP | 200464087 A | 2/2004 |
| JP | 2005337962 A | 12/2005 |
| JP | 200848910 A | 3/2008 |
| JP | 2009133837 A | 6/2009 |

(Continued)

OTHER PUBLICATIONS

Written Opinion, dated Mar. 13, 2012, issued by the International Searching Authority in International Application No. PCT/JP2012/053970.

(Continued)

*Primary Examiner* — Casey Bryant
(74) *Attorney, Agent, or Firm* — Sughrue Mion, PLLC

(57) ABSTRACT

An adiological image detection apparatus 3 includes a phosphor 60 that contains a fluorescent material which emits fluorescence by radiation exposure, and a sensor panel 61 which is provided to be in close contact with the phosphor, and detects the fluorescence emitted from the phosphor. The phosphor includes a columnar section that is formed by a group of columnar crystals 82 formed by growing crystals of the fluorescent material in a columnar shape, a radiation incident plane is provided in the sensor panel at a side opposite to the phosphor, and the sensor panel has flexibility and is curved to locate a curvature center at the radiation incident plane side.

17 Claims, 20 Drawing Sheets

(56) References Cited

FOREIGN PATENT DOCUMENTS

| JP | 2009136518 A | 6/2009 |
| JP | 2009236704 A | 10/2009 |
| JP | 201025620 A | 2/2010 |
| JP | 201117683 A | 1/2011 |
| WO | 2010095188 A1 | 8/2010 |

OTHER PUBLICATIONS

International Search Report, dated Mar. 13, 2012, issued by the International Searching Authority in International Application No. PCT/JP2012/053970.

* cited by examiner

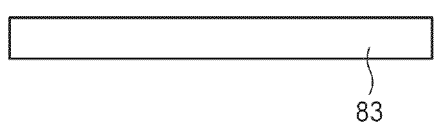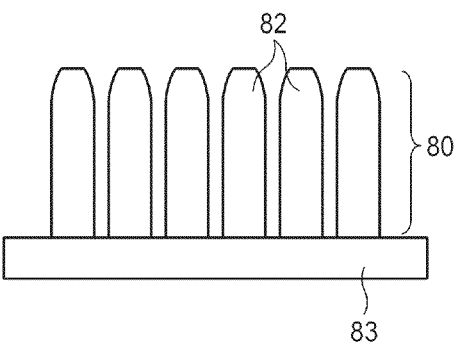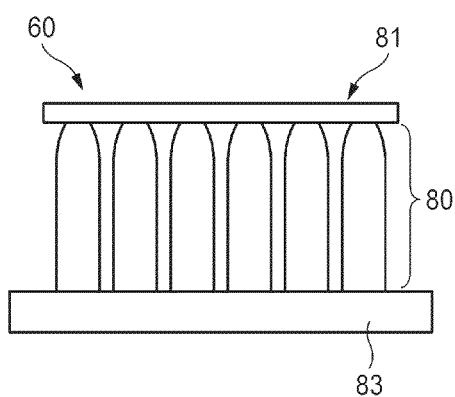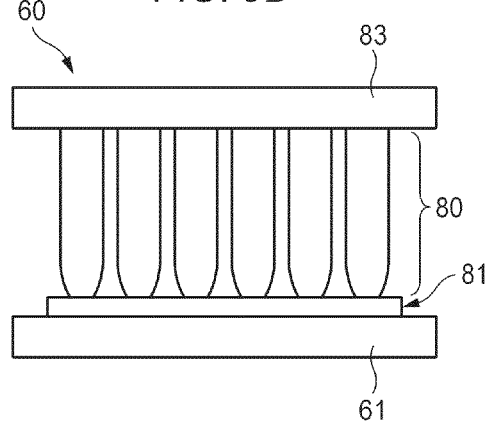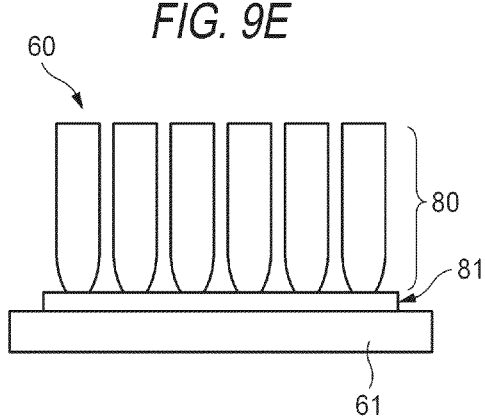

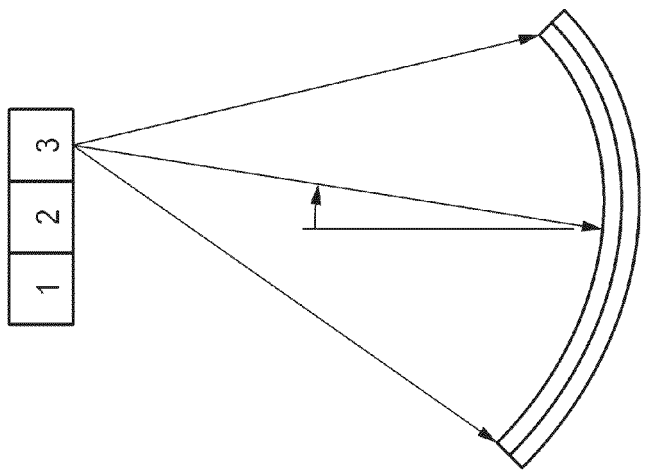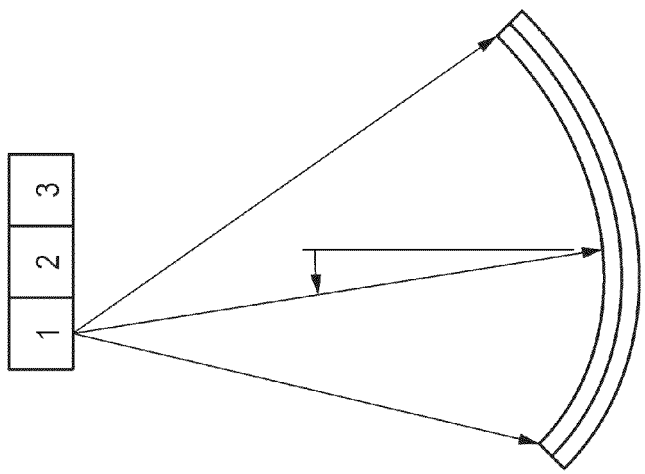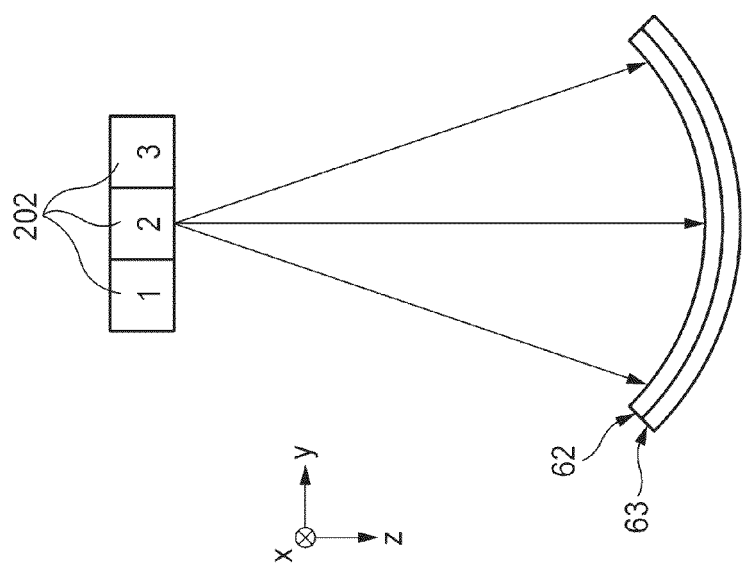

RADIOLOGICAL IMAGE DETECTION APPARATUS AND RADIATION IMAGING APPARATUS

CROSS REFERENCE TO RELATED APPLICATIONS

This is a continuation of International Application No. PCT/JP2012/053970 filed Feb. 20, 2012, which claims priority from Japanese Patent Application No. 2011-035227 filed Feb. 20, 2011, the contents of all of which are incorporated herein by reference.

TECHNICAL FIELD

The present invention relates to a radiological image detection apparatus and a radiation imaging apparatus.

BACKGROUND ART

In recent years, a radiological image detection apparatus using an FPD (Flat Panel Detector) for detecting a radiological image to generate digital image data has been put to practical use, and is being widely used rapidly due to a merit that an image may be confirmed in real time as compared with a conventional imaging plate. There are various types of such radiological image detection apparatuses. As one example, an indirect conversion type has been known.

The indirect conversion type of radiological image detection apparatus includes a scintillator formed by a fluorescent material which emits fluorescence by radiation exposure, such as CsI or NaI, and a sensor panel which has two-dimensionally arrayed photoelectric conversion elements. Radiation transmitted through a subject is firstly converted into light by the scintillator, and the fluorescence of the scintillator is photoelectrically converted by a group of photoelectric conversion elements of the sensor panel, thereby generating an electrical signal (digital image data).

In the radiological image detection apparatus, there is also known a technology for forming a scintillator by a group of columnar crystals of a fluorescent material such as CsI for the purpose of improving the sensitivity (e.g., see Patent Literature 2). The columnar crystals are typically formed by growing crystals of the fluorescent material into columnar shapes on a support by a vapor deposition method. As the support, a sensor panel or a suitable substrate is used. When the sensor panel is used as the support, a group of columnar crystals are directly formed on the sensor panel. Also, when a suitable substrate is used as the support, a group of columnar crystals formed on the substrate are bonded to the sensor panel. The columnar crystals formed by the vapor deposition method do not include impurities such as a binder, and also have a light guide effect which guides fluorescence generated in the columnar crystals in the crystal growth direction, thereby suppressing the fluorescence from being diffused. This improves the sensitivity of the radiological image detection apparatus, and also improves the sharpness of an image.

The columnar crystals are grown almost perpendicularly to the surface of the support. Thus, in the case of bonding the group of the columnar crystals formed on the substrate to the sensor panel as well as in the case of using the sensor panel as the support, the respective columnar crystals are provided almost perpendicularly to the surface of the sensor panel. When the sensor panel is flat, radiation has a large incident angle with respect to the columnar crystals provided perpendicularly to the surface of the sensor panel so that it may be deviated from the center of the irradiation field. Thus, the radiation proceeds through a plurality of columnar crystals, thereby lowering the sharpness of an image.

Therefore, in the radiological image detection apparatus disclosed in Patent Literature 2, a flexible sensor panel is used, in which the sensor panel is curved so that respective columnar crystals may be parallel to radiation which is radially widened. In each portion of the irradiation field, the respective columnar crystals become parallel to the radiation, thereby suppressing sharpness of an image from being lowered.

CITATION LIST

Patent Literature

Patent Literature 1: JP-A-2010-025620
Patent Literature 2: JP-A-2011-017683
Patent Literature 3: JP-A-2004-064087

SUMMARY OF INVENTION

Technical Problem

The radiological image detection apparatus disclosed in Patent Literature 2 is a so-called reverse side readout (PSS: Penetration Side Sampling) type of radiological image detection apparatus in which radiation is incident from a scintillator side. In the PSS type of radiological image detection apparatus, when the sensor panel is curved so that the respective columnar crystals of the scintillator may be parallel to the radiation, a gap between front end portions of the group of columnar crystals may become narrower, and front end portions of adjacent columnar crystals may be damaged by coming in contact with each other. Accordingly, the radius of curvature at the time of curving the sensor panel is limited. Thus, when an imaging distance (SID: Source-Image Distance) is relatively short, the respective columnar crystals may not be disposed to be parallel to the radiation, which makes it difficult to sufficiently achieve the sharpness of an image.

The present invention has been made in consideration of the foregoing problems, and an object thereof is to suppress a phosphor from being damaged when a sensor panel of a radiological image detection apparatus is curved to improve the sharpness of an image.

Solution to Problem (1) A radiological image detection apparatus includes: a phosphor which contains a fluorescent material that emits fluorescence by radiation exposure, and a sensor panel which is provided to be in close contact with the phosphor, and detects the fluorescence emitted from the phosphor, in which the phosphor includes a columnar section that is formed by a group of columnar crystals formed by growing crystals of the fluorescent material in a columnar shape, a radiation incident plane is provided in the sensor panel at a side opposite to the phosphor, and the sensor panel has flexibility and is curved to locate a curvature center at the side of the radiation incident plane.

(2) A radiation imaging apparatus includes: the radiological image detection apparatus of (1); and a radiation source configured to irradiate radiation toward the radiological image detection apparatus, wherein the curvature center of the sensor panel corresponds to a focal point of the radiation source.

Advantageous Effects of Invention

According to the present invention, with respect to the sensor panel that is curved to locate the center of curvature at radiation incident plane side, the phosphor is disposed at the outer diameter side, and gaps between front end portions of the group of columnar crystals constituting the phosphor are widened. Accordingly, front end portions of the adjacent columnar crystals are avoided from coming in contact with each other, thereby suppressing the columnar crystals from being damaged. Thus, even if an imaging distance is relatively short, the respective columnar crystals may be disposed to be parallel to radiation in accordance with the imaging distance, thereby improving the sharpness of an image.

BRIEF DESCRIPTION OF DRAWINGS

FIGS. 9A to 9E are views illustrating another example of a method of manufacturing the detection unit in FIG. 3.

FIGS. 19A to 19C are views illustrating a state where a detection unit of the radiological image detection apparatus in FIG. 18 is curved.

DESCRIPTION OF EMBODIMENTS

Figure 1:
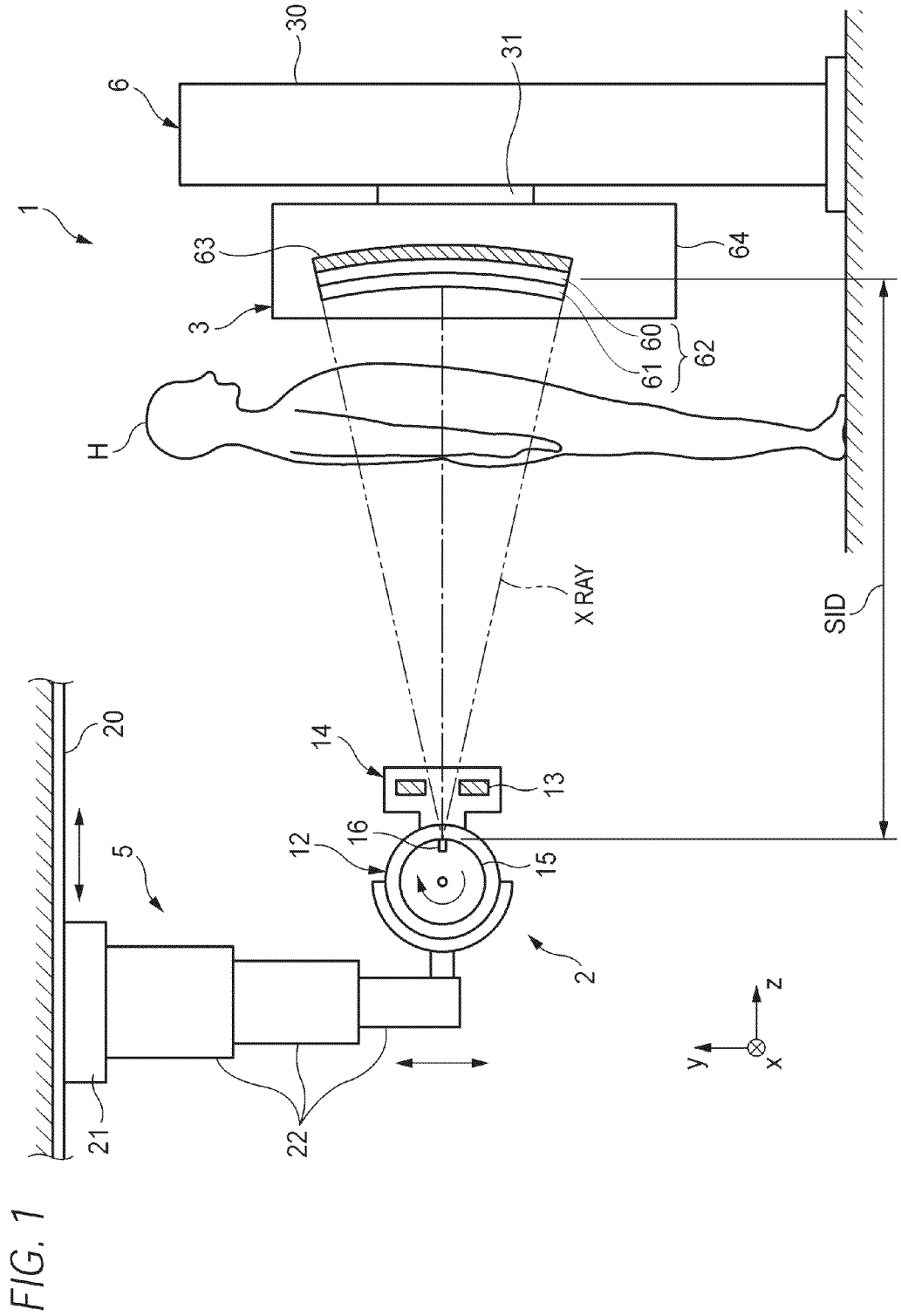
FIG. 1 is a view illustrating a configuration of an example of a radiological image detection apparatus and a radiation imaging apparatus for describing an exemplary embodiment of the present invention.
Figure 2:
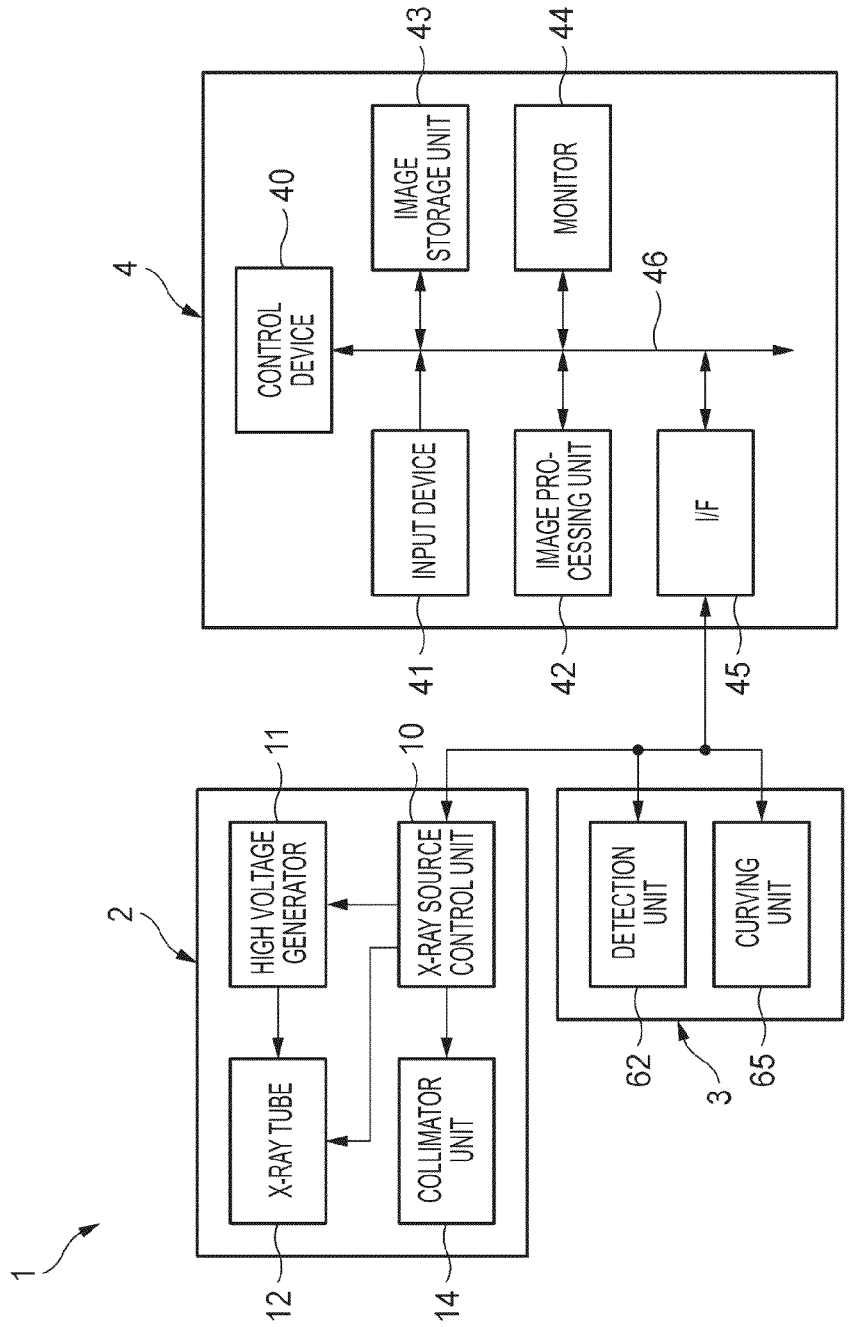
FIG. 2 is a view illustrating a control block of the radiation imaging apparatus in FIG. 1.

FIG. 1 illustrates a configuration of an example of a radiological image detection apparatus and a radiation imaging apparatus for describing an exemplary embodiment of the present invention, and FIG. 2 illustrates a control block of the radiation imaging apparatus in FIG. 1.

An X-ray imaging apparatus 1 is an X-ray diagnosis apparatus for imaging a subject (patient) H in upright position, and is largely divided into an X-ray source 2 which emits cone beam X-rays to the subject H, an X-ray image detection apparatus 3 which is disposed oppositely to the X-ray source 2 and detects the X-rays transmitted through the subject H from the X-ray source 2 to generate image data, and a console 4 which controls the exposure operation of the X-ray source 2 or the imaging operation of the X-ray image detection apparatus 3 based on the operation of an operator while processing the image data obtained by the X-ray image detection apparatus 3. The X-ray source 2 is held by an X-ray source holding device 5 which is suspended from the ceiling. The X-ray image detection apparatus 3 is held by a stand 6 placed on the floor.

The X-ray source 2 includes an X-ray tube 12 configured to generate the X-rays according to a high voltage applied from a high voltage generator 11 based on the control of an X-ray source control unit 10, and a collimator unit 14 having a movable collimator 13 which limits the irradiation field to shield a part having no contribution to the inspection area of the subject H, among the X-rays generated from the X-ray tube 12. The X-ray tube 12 is of a rotary anode type, which emits an electron beam from a filament (not illustrated) as an electron emitting source (cathode), and collids the electron beam with a rotary anode 15 that rotates at a predetermined speed so as to generate the X-rays. The portion of the rotary anode 15 which collids with the electron beam becomes an X-ray focal point 16.

The X-ray source holding device 5 includes a carriage unit 21 configured to be movable in the horizontal direction (the z direction) along a ceiling rail 20 provided on the ceiling, a plurality of struts 22 which are connected to each other and extend and retract downwardly from the carriage unit 21, a driving mechanism configured to move the carriage unit 21 along the ceiling rail, and a driving mechanism configured to extend/retract the struts 22. The X-ray source 2 is attached to the leading end of the struts 22. While the X-ray source holding device 5 is moved along the ceiling rail 20, a distance SID between the X-ray source 2 and the X-ray image detection apparatus 3 with respect to the horizontal direction is varied. Also, while the struts 22 are extended/retracted, the position of the X-ray source 2 with respect to the vertical direction is varied. Both the driving mechanisms are controlled by the console 4 based on the setting operations of an operator.

The X-ray source holding device 5 is provided with a position sensor (not illustrated) such as a potentiometer, which measures the moving amount of the carriage unit 21 along the ceiling rail, thereby detecting the position of the X-ray source 2 with respect to the horizontal direction. The detection value of the position sensor is supplied to the console 4 via a wired or wireless communication.

The stand 6 includes a main body 30 provided at the floor, a holding part 31 which is vertically movably attached to the main body 30, and a driving mechanism configured to vertically move the holding part 31. The X-ray image detection apparatus 3 is attached to the holding part 31. The driving mechanism is controlled by a control device 40 of the console 4 to be described later based on the setting operations of an operator.

The stand 6 is provided with a position sensor (not illustrated) such as a potentiometer, which measures the moving amount of the holding part 31, thereby detecting the position of the X-ray image detection apparatus 3 with respect to the vertical direction. The detection value of the position sensor is supplied to the console 4 via a wired or wireless communication.

In the console 4, the control device 40 including, for example, CPU, ROM, and RAM is provided. The control device 40 includes an input device 41 to which an operator inputs an imaging command or the contents of the command, an image processing unit 42 configured to process the image data obtained by the X-ray image detection apparatus 3 to generate an X-ray image, an image storage unit 43 configured to store the X-ray image, a monitor 44 configured to display, for example, the X-ray image, and an interface (I/F) 45 connected to respective units of the X-ray imaging apparatus 1. The control device 40, the input device 41, the image processing unit 42, the storage unit 43, the monitor 44, and the I/F 45 are connected via a bus 46.

Through the operation of the input device 41, for example, an X-ray imaging condition such as a distance (imaging distance) SID between the X-ray source 2 and the X-ray image detection apparatus 3, or a tube voltage, and an imaging timing are input. The control device 40 drives the X-ray source holding device 5 to move the X-ray source 2 to a position corresponding to the input imaging distance SID based on the horizontal position of the X-ray source 2 which is provided from the X-ray source holding device 5. Also, the control device 40 drives the X-ray source holding device 5 to move the X-ray source 2 to a vertical position opposite to the X-ray image detection apparatus 3 based on the vertical position of the X-ray image detection apparatus 3 which is provided from the stand 6.

The X-ray image detection apparatus 3 includes a scintillator (phosphor) 60 that contains a fluorescent material which emits fluorescence by X-ray exposure, and a sensor panel 61 which has two-dimensionally arrayed photoelectric conversion elements 70 that photoelectrically converts the fluorescence emitted from the scintillator 60. The scintillator 60 is adhered to the sensor panel 61 via a resin layer that optically couples the scintillator 60 with a group of the photoelectric conversion elements 70. A detection unit 62 that includes the scintillator 60 adhered to the sensor panel 61 is supported by a support 63 and housed within a case 64.

Hereinafter, the detection unit 62 will be described.

Figure 3:
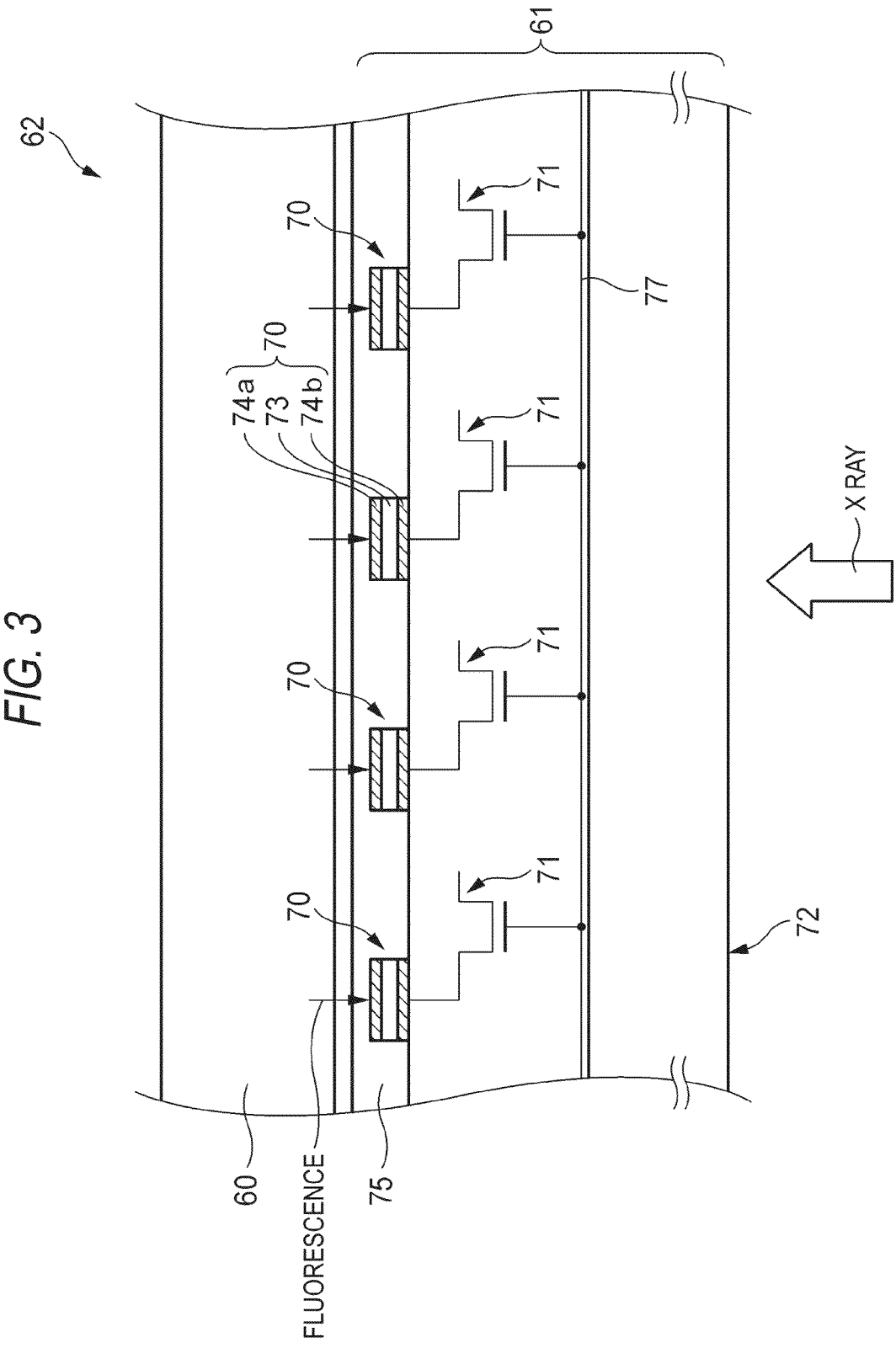
FIG. 3 is a view illustrating a configuration of a detection unit of the radiological image detection apparatus for describing an exemplary embodiment of the present invention.
Figure 4:
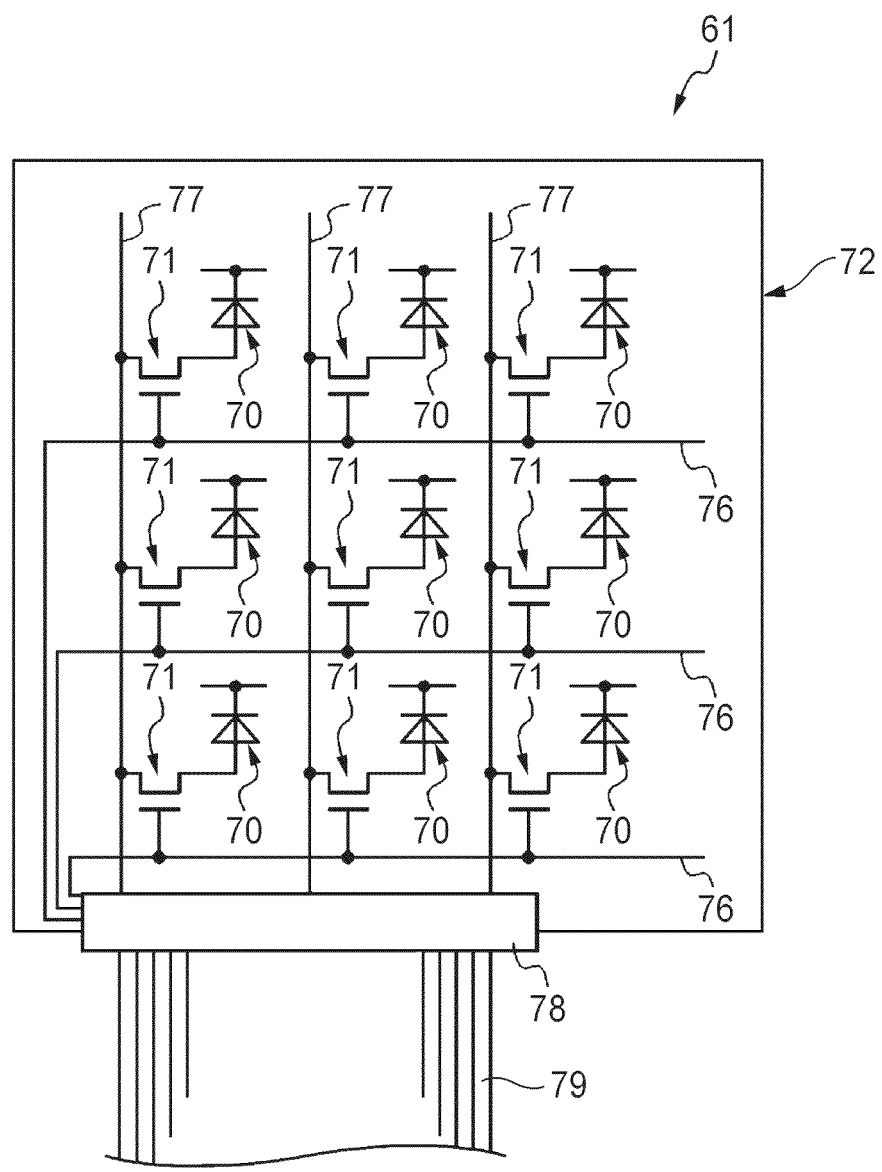
FIG. 4 is a view illustrating a configuration of a sensor panel of the detection unit in FIG. 3.

FIG. 3 schematically illustrates a configuration of the detection unit 62, and FIG. 4 schematically illustrates a configuration of the sensor panel 61 of the detection unit 62.

The detection unit 62 is a so-called ISS-type detection unit. In the sensor panel 61 bonded to the scintillator 60, the sensor panel 61 is disposed at the X-ray source 2 side. X-rays are transmitted through the sensor panel 61 and incident on the scintillator 60. The scintillator 60 on which the X-rays are incident emits fluorescence, and the emitted fluorescence is photoelectrically converted by the group of photoelectric conversion elements 70 of the sensor panel 61. In the X-ray image detection apparatus 3 as configured above, the radiation incident side of the scintillator 60 which emits a lot of fluorescence is provided adjacently to the sensor panel 61, thereby improving the sensitivity.

The sensor panel 61 has a flexible TFT substrate 72 in which switching devices 71 consisting of TFTs (Thin Film Transistors) are formed on an insulating flexible substrate. The group of photoelectric conversion elements 70 are formed on the flexible TFT substrate 72. On the flexible TFT substrate 72, a flattening layer 75 is formed to cover the group of photoelectric conversion elements 70, and flatten the surface of the flexible TFT substrate 72. The flattening layer 75 is included in the above described resin layer which optically couples the scintillator 60 with the group of photoelectric conversion elements 70. As for resin for the flattening layer 75, for example, polyimide or parylene may be used, and it is preferable to use polyimide with a good film-forming property. Also, the thickness of the resin layer is preferably 50 μm or less, and more preferably from 5 μm to 30 μm from the standpoints of sensitivity and image sharpness.

Each of the photoelectric conversion elements 70 includes a photoconductive layer 73 on which the fluorescence of the scintillator 60 is incident to generate electric charges, and a pair of electrodes provided on the front and rear surfaces of the photoconductive layer 73. An electrode 74a provided on the scintillator 60 side surface of the photoconductive layer 73 is a bias electrode configured to apply a bias voltage to the photoconductive layer 73, and an electrode 74b provided on the opposite surface is a charge collection electrode configured to collect the electric charges generated by the photoconductive layer 73.

The switching devices 71 are two-dimensionally arrayed to correspond to the two-dimensionally arrayed photoelectric conversion elements 70, on the flexible TFT substrate 72. The charge collection electrode 74b of each of the photoelectric conversion elements 70 is connected to the corresponding switching device 71. The electric charges collected by the charge collection electrode 74b are read out through the switching device 71.

A plurality of gate lines 76 and a plurality of signal lines 77 are provided in the flexible TFT substrate 72. The gate lines 76 extend in one direction (row direction) to switch on/off the respective switching devices, and the signal lines 77 extend in the direction (column direction) perpendicular to the gate lines 76 to read out the electric charges through the switching devices 71 which are switched to ON state. A connection terminal 78 connected to the respective gate lines 76 and the respective signal lines 77 is disposed at a peripheral edge of the flexible TFT substrate 72. The connection terminal 78 is connected to a circuit board (not illustrated) via a connection circuit 79. The circuit board has a gate driver as an external circuit, and a signal processing unit.

The switching devices 71 are sequentially switched to ON state line by line by a signal supplied via the gate lines 76 from the gate driver. The electric charges read out by the switching devices 71 which are switched to the ON state are transmitted via the signal lines 77, and input to the signal processing unit. Accordingly, the electric charges are sequentially read out line by line, and converted into an electrical signal in the signal processing unit to generate digital image data.

Hereinafter, the scintillator 60 will be described.

Figure 5:
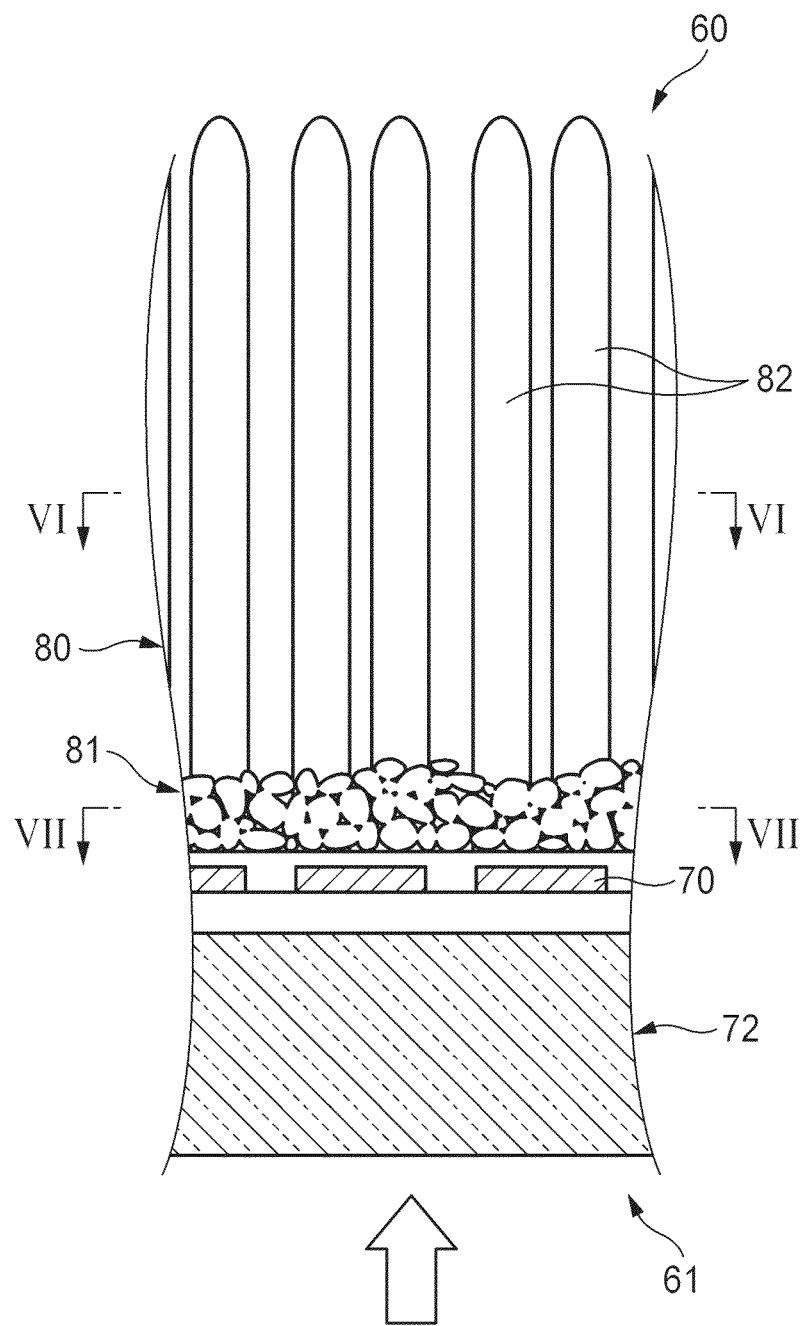
FIG. 5 is a view illustrating a configuration of a phosphor of the detection unit in FIG. 3.

FIG. 5 schematically illustrates a configuration of the scintillator 60.

As for the fluorescent material that forms the scintillator 60, for example, CsI:Tl (thallium-activated cesium iodide), NaI:Tl (thallium-activated sodium iodide), or CsI:Na (sodium-activated cesium iodide) may be used. Among them, CsI:Tl is preferable in view of the fact that the light emission spectrum is suitable for the maximum value (around 550 nm) of the spectral sensitivity of an a-Si photodiode.

The scintillator 60 includes a columnar section 80 and a non-columnar section 81 provided at the sensor panel side of the columnar section 80. The columnar section 80 and the non-columnar section 81 are continuously stacked in layers, and may be formed by a vapor deposition method which will be described later. In the scintillator 60, the non-columnar section 81 is adhered to the sensor panel 61.

The columnar section 80 is formed by a group of columnar crystals 82 formed by growing crystals of the above described fluorescent material in a columnar shape. Each of the columnar crystals 82 is provided substantially perpendicularly to the surface of the sensor panel 61. A gap is interposed between adjacent columnar crystals 82, and the respective columnar crystals 82 exist independently of each other.

The non-columnar section 81 is formed by a group of relatively small crystals of the fluorescent material. In the non-columnar section 81 formed by the group of crystals each having a relatively small diameter, the crystals are irregularly bonded to each other or overlap each other, and thus clear gaps between the crystals hardly occur. Also, in the non-columnar section 81, an amorphous form of the fluorescent material may be included.

The fluorescence generated in each of the columnar crystals 82 is suppressed from diffusing since total reflection within the columnar crystal 82 is repeated due to the difference in refractive index between the columnar crystal 82 and the gap (air) around the crystal. Then, the fluorescence is guided to the photoelectric conversion element 70 opposed to the columnar crystal 82. Accordingly, the sharpness of an image is improved.

The non-columnar section 81 formed by the crystals each having a relatively small diameter or aggregates thereof is dense and has a low porosity as compared to the columnar section 80. Since in the scintillator 60, the non-columnar section 81 is adhered to the sensor panel 61, adhesion between the scintillator 60 and the sensor panel 61 is improved. This suppresses the scintillator 60 from being peeled off from the sensor panel 61.

Figure 6:
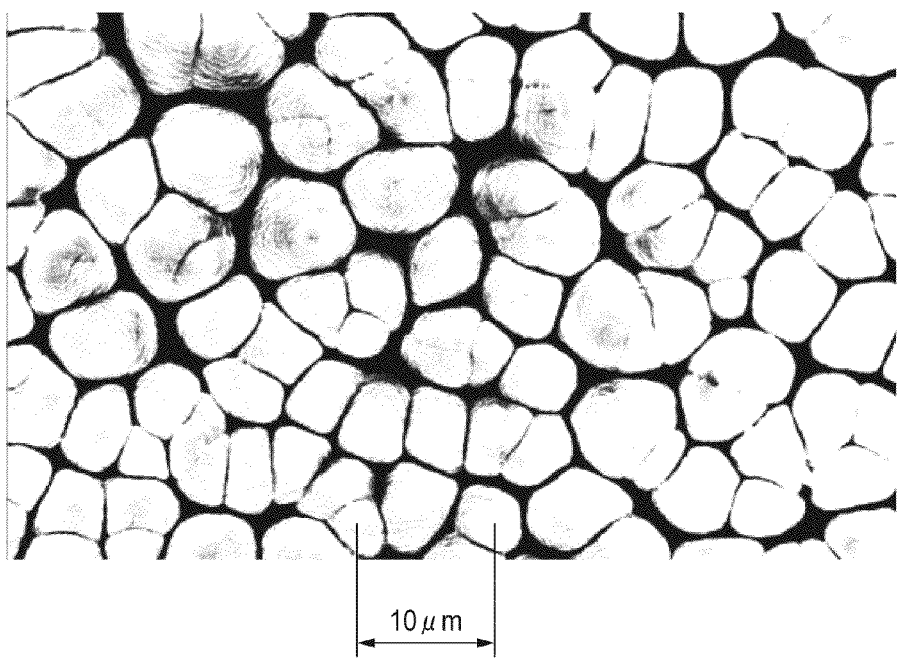
FIG. 6 is a view illustrating a section taken along line VI-VI of the phosphor in FIG. 5.

FIG. 6 is an electron microscopic photograph illustrating a section taken along VI-VI of the scintillator 60 in FIG. 5.

As is obvious from FIG. 6, in the columnar section 80, the columnar crystals 82 show a substantially uniform cross-sectional diameter in the crystal growth direction, and also, the columnar crystals 82 exist independently of each other with gaps around the columnar crystals 82. The crystal diameter (columnar diameter) of the columnar crystals 82 preferably ranges from 2 µm to 8 µm from the viewpoints of a light guide effect, a mechanical strength, and a pixel defect prevention. When the crystal diameter is too small, the columnar crystals 82 may lack the mechanical strength, and thus may be damaged by, for example, shock. When the crystal diameter is too large, the number of the columnar crystals 82 in each of the photoelectric conversion elements 70 may be decreased. Thus, if a crack occurs in the crystals, the probability of forming defects in the corresponding element may increase.

Here, the columnar diameter refers to a maximum diameter of a crystal when observed from the top plan in the growing direction of the columnar crystals 82. In a specific measuring method, the columnar diameter is measured by observation from the top plan in the growing direction of the columnar crystals 82 with an SEM (scanning electron microscope). Observation is performed with a magnification (about 2,000×) that allows 100 to 200 columnar crystals 82 to be observed, and then a value obtained by measuring and taking an average on the maximum values of columnar diameters obtained for all the crystals included at one shot is employed. The columnar diameters (µm) are read to two decimal places, and the average value is determined by rounding off to one decimal place in accordance with JIS Z 8401.

The thickness of the columnar section 80 depends on the energy of radiation, but preferably ranges from 200 µm to 700 µm from the viewpoints of sufficient radiation absorption and image sharpness in the columnar section 80. When the thickness of the columnar section 80 is too small, radiation may not be sufficiently absorbed, and thus the sensitivity may deteriorate. When the thickness is too large, light diffusion may occur, and thus the image sharpness may deteriorate even by the light guide effect of the columnar crystals.

Figure 7:
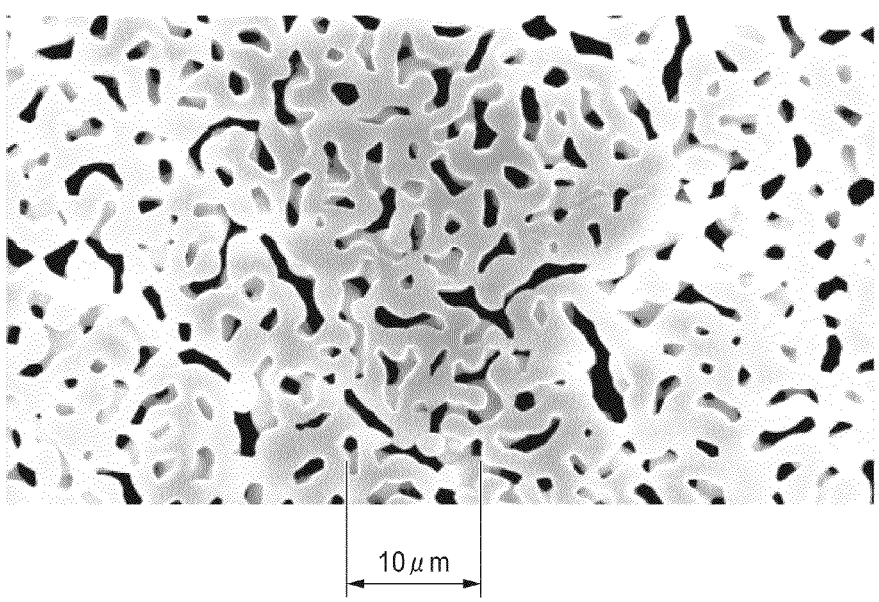
FIG. 7 is a view illustrating a section taken along line VII-VII of the phosphor in FIG. 5.

FIG. 7 is an electron microscopic photograph illustrating a section taken along VII-VII of the scintillator 60 in FIG. 5.

As is obvious from FIG. 7, in the non-columnar section 81, since the crystals are irregularly bonded to each other or overlap each other, a clear gap between the crystals is not confirmed unlike in the columnar section 80. The diameter of the crystals constituting the non-columnar section 81 is preferably 7.0 µm or less from the viewpoint of adhesion. When the crystal diameter is too large, the flatness may deteriorate and thus, the adhesion with the sensor panel 61 may deteriorate.

Here, in a case where crystals are bonded to each other, the crystal diameter is measured as follows. A line connecting concave portions (recesses) occurring between adjacent crystals is considered as a boundary between the crystals, and the bonded crystals are separated to be the smallest polygons so that a columnar diameter and a crystal diameter corresponding to the columnar diameter are measured. Then, the average value thereof is determined and is employed in the same manner as the crystal diameter of the columnar section 80.

The thickness of the non-columnar section 81 preferably ranges from 5 µm to 50 µm from the viewpoints of the adhesion with the sensor panel 61 and the image quality. When the thickness of the non-columnar section 81 is too small, a sufficient adhesion with the sensor panel 61 may not be achieved. When the thickness is too large, contribution of the fluorescence to the non-columnar section 81, and diffusion of the fluorescence in the non-columnar section 81 may be increased and thus, the image sharpness may deteriorate.

Hereinafter, a method of manufacturing the foregoing scintillator 60 will be described.

Figure 8A:
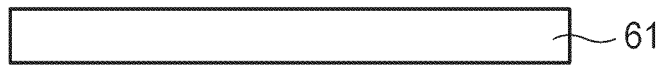
FIGS. 8A to 8C are views illustrating an example of a method of manufacturing the detection unit in FIG. 3.
Figure 8B:
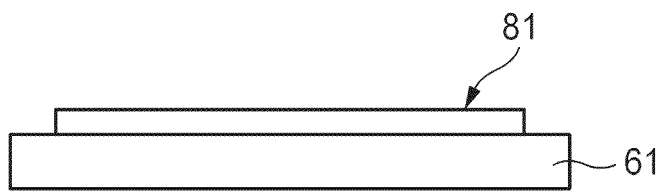
Figure 8C:
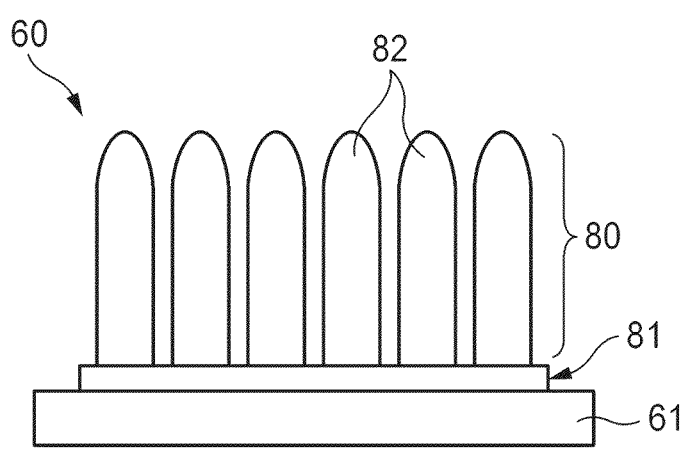

FIGS. 8A to 8C schematically illustrate an example of a method of manufacturing the scintillator 60.

In the method of manufacturing the scintillator 60, as illustrated in FIGS. 8A to 8C, the scintillator 60 is directly formed on the surface of the sensor panel 61 by a vapor deposition method. By the vapor deposition method, the columnar section 80 and the non-columnar section 81 may be continuously and integrally formed. Hereinafter, a case in which CsI:Tl is used as a fluorescent material will be described by way of an example.

In forming the scintillator 60 by the vapor deposition method, under the environment with a degree of vacuum of, for example, 0.01 to 10 Pa, CsI:Tl is heated and vaporized, for example, by means of applying an electric current to a resistance heating crucible, and then the temperature of the sensor panel 61 is adjusted to room temperature (20° C.) to 300° C. so as to deposit CsI:Tl on the sensor panel 61.

When the crystalline phase of CsI:Tl is formed on the sensor panel 61, at the initial stage, crystals each having a relatively small diameter are deposited to form the non-columnar section 81 (FIG. 8B). Then, by varying at least one condition of the degree of vacuum, and the temperature of the sensor panel 61, the columnar section 80 is formed in succession after the non-columnar section 81 is formed. Specifically, the columnar crystals 82 are grown by increasing the degree of vacuum, and/or increasing the temperature of the sensor panel 61 (FIG. 8C).

The detection unit 62 is configured in this manner in which the scintillator 60 that includes the non-columnar section 81 adhered to the sensor panel 61 is formed on the sensor panel 61.

FIGS. 9A to 9E schematically illustrate another example of a method of manufacturing the scintillator 60.

In the method of manufacturing the scintillator 60, as illustrated in FIGS. 9A to 9E, a substrate 83 is used, in which the scintillator 60 is formed on the surface of the substrate 83, and then the scintillator 60 formed on the substrate 83 is bonded to the sensor panel 61.

Examples of the substrate 83 that may be used may include a carbon plate, a CFRP (Carbon Fiber Reinforced Plastic), a glass plate, a quartz substrate, a sapphire substrate, and a metal sheet made of, for example, iron, tin, chromium, or aluminum, but are not limited thereto as long as the scintillator 60 may be formed on the substrate.

In the present example, the scintillator 60 is also formed by the vapor deposition method. Under the environment with a degree of vacuum of 0.01 to 10 Pa, CsI:Tl is heated and vaporized, for example, by means of applying an electric current to a resistance heating crucible, and then the temperature of the support is adjusted to room temperature (20° C.) to 300° C. so as to deposit CsI:Tl on the substrate 83.

When the crystalline phase of CsI:Tl is formed on the substrate 83, at the initial stage, the columnar crystals 82 are grown to form the columnar section 80 (FIG. 9B). Then, by decreasing the degree of vacuum and/or lowering the temperature of the substrate 83, the non-columnar section 81 is formed in succession after forming the columnar section 80 (FIG. 9C).

After the scintillator 60 is formed on the substrate 83, an adhesive layer is interposed to adhere the non-columnar section 81 of the scintillator 60 to the sensor panel 61 (FIG. 9D). Then, the detection unit 62 is configured by peeling off the substrate 83 (FIG. 9E). There is no particular limitation in the adhesive layer as long as it allows the fluorescence from the scintillator 60 to reach the sensor panel 61 without being attenuated. For example, the adhesive layer may be formed by an adhesive such as a UV curable adhesive, a heat curing adhesive, a room temperature setting adhesive or a hot melt adhesive, a cohesive agent such as a rubber-based cohesive agent, a silicon-based cohesive agent, or an acrylic cohesive agent, or a double-sided adhesive/cohesive sheet provided with the adhesive agents or the cohesive agents on both surfaces thereof. Also, as for the adhesive, from the viewpoint of suppressing the sharpness of an image from deteriorating, it is preferable to use an adhesive made of a low-viscosity epoxy resin because it may form a sufficiently thin adhesive layer with respect to an element size. Also, as for the cohesive agent, an acrylic cohesive agent which is deteriorated less by light or oxidation is preferred. When the scintillator 60 and the sensor panel 61 are adhered to each other by the adhesive layer, the adhesive layer is included in the above described resin layer which optically couples the scintillator 60 with the group of photoelectric conversion elements 70 of the sensor panel 61.

The X-ray image detection apparatus 3 further includes a curving unit 65 configured to curve the detection unit 62 as configured above. Hereinafter, the curving unit 65 will be described.

Figure 10:
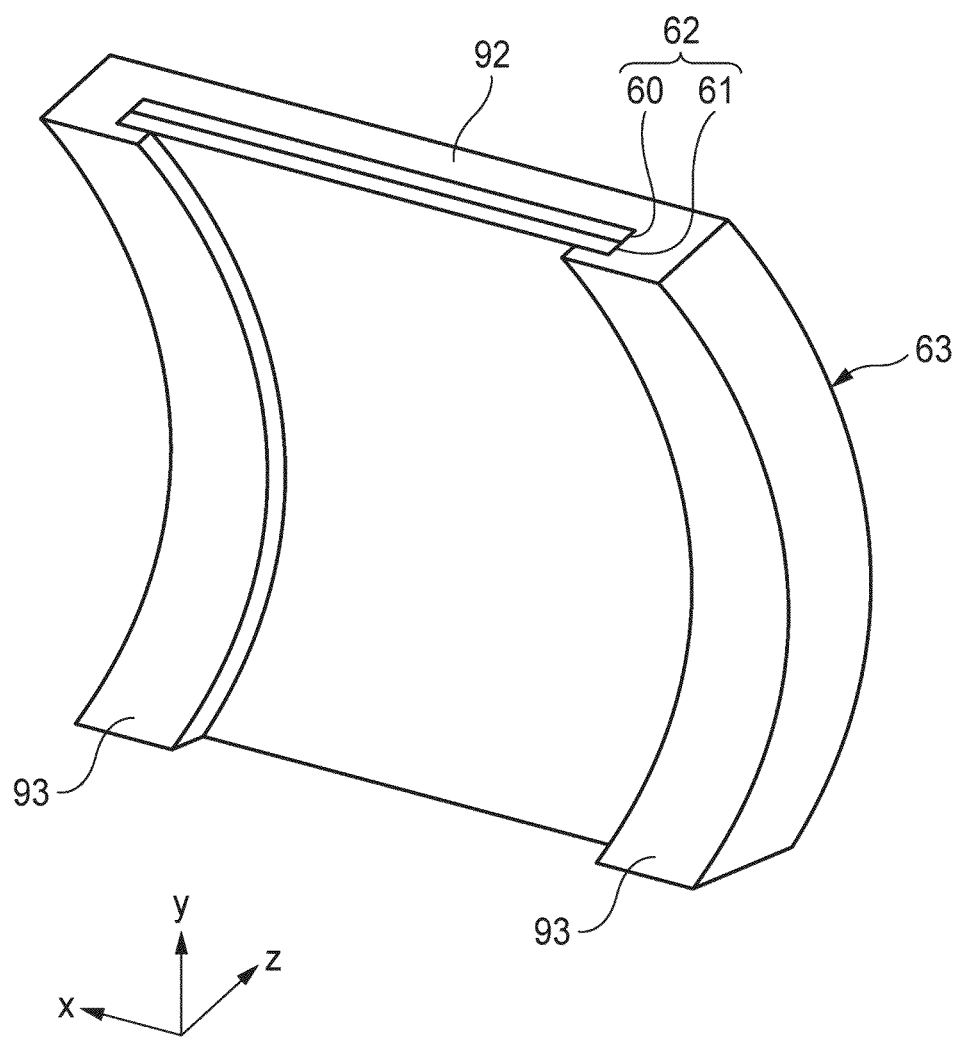
FIG. 10 is a view illustrating a configuration of a curving unit of the radiological image detection apparatus in FIG. 1.
Figure 11:
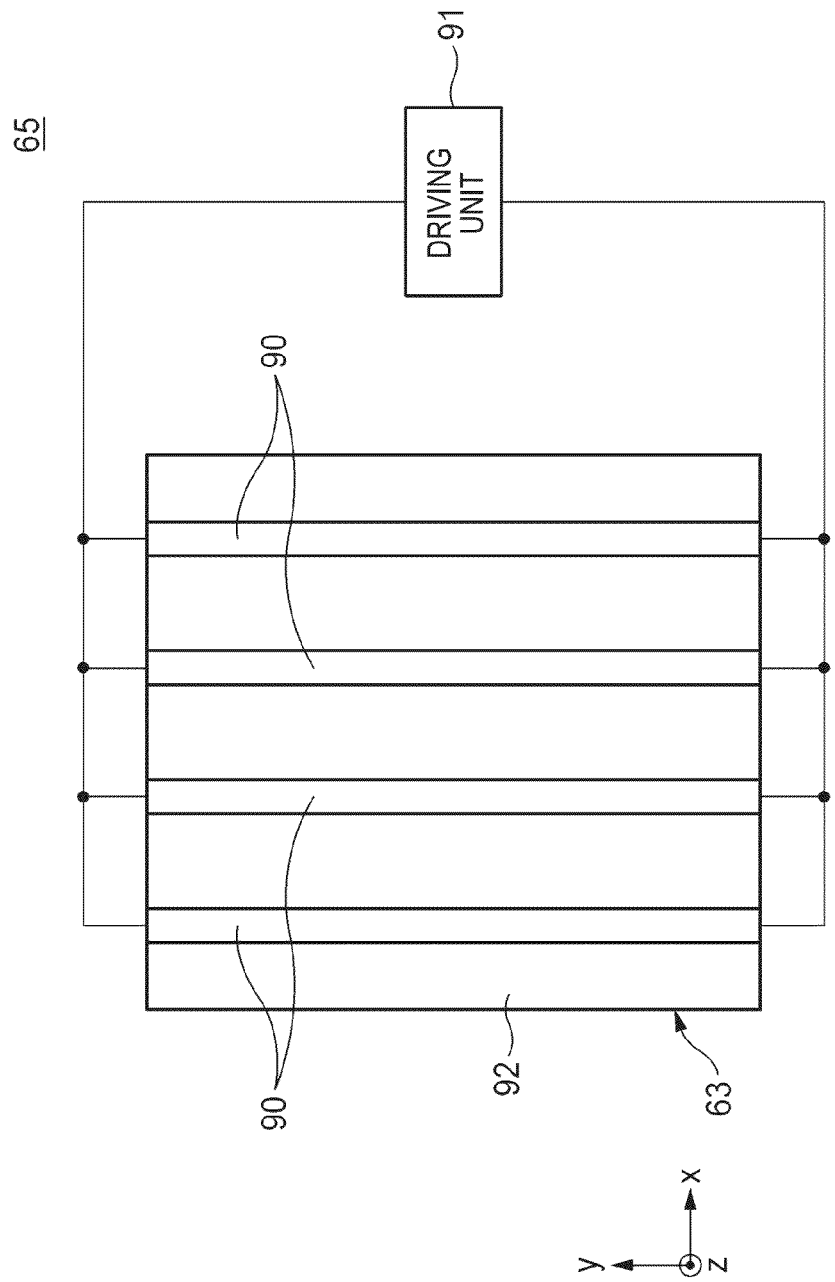
FIG. 11 is a view illustrating a configuration of the curving unit in FIG. 10.

FIGS. 10 and 11 illustrate the configuration of the curving unit 65.

The curving unit 65 includes the support 63 configured to support the detection unit 62, driven members 90 which are disposed in the support 63 and curved by physical stimulation, and a driving unit 91 configured to apply the physical stimulation to the driven members 90.

The support 63 includes a cover part 92 which has a light shielding property, and covers the scintillator 60 side of the detection unit 62, that is, the side opposite to the X-ray incident side, and engaging parts 93 configured to engage a pair of edges of the detection unit 62 (a pair of edges in the y direction in the illustrated example). The support 63 is made of a material which has a flexibility that allows the material to be self-supporting, for example, a rubber-based or pitch-based carbon fiber may be suitably used.

As for the driven members 90, in the present example, band-shaped bimetals 90 which are configured to be curved by heat as the physical stimulation are used. The plurality of bimetals 90 are affixed on the rear surface of the cover part 92, and are provided to extend in parallel to each other in the y direction, and to be spaced apart from each other at a suitable interval in the x direction.

The driving unit 91 applies a suitable electric current to each of the bimetals 90. The bimetal 90 applied with the electric current from the driving unit 91 is curved by self-heating due to its resistance so as to locate the center of curvature at the X-ray incident side of the detection unit 62. Then, the driving unit 91 is configured to apply the electric current to each of the bimetals 90 in accordance with an imaging distance SID set by the console 4, and the bimetal 90 applied with the electric current from the driving unit 91 is curved so as to substantially conform to the cylindrical surface around a center axis which is a straight line in parallel to the x direction passing through the X-ray focal point 16.

In concurrence with the curving of the bimetals 90, the support 63 and the detection unit 62 supported by the support 63 are also curved. Since the bimetals 90 are curved to substantially conform to the cylindrical surface around a center axis which is a straight line in parallel to the x direction passing through the X-ray focal point 16, the detection unit 62 is also curved in the same manner, and its center of curvature is disposed at a position substantially corresponding to the X-ray focal point 16.

Figure 12:
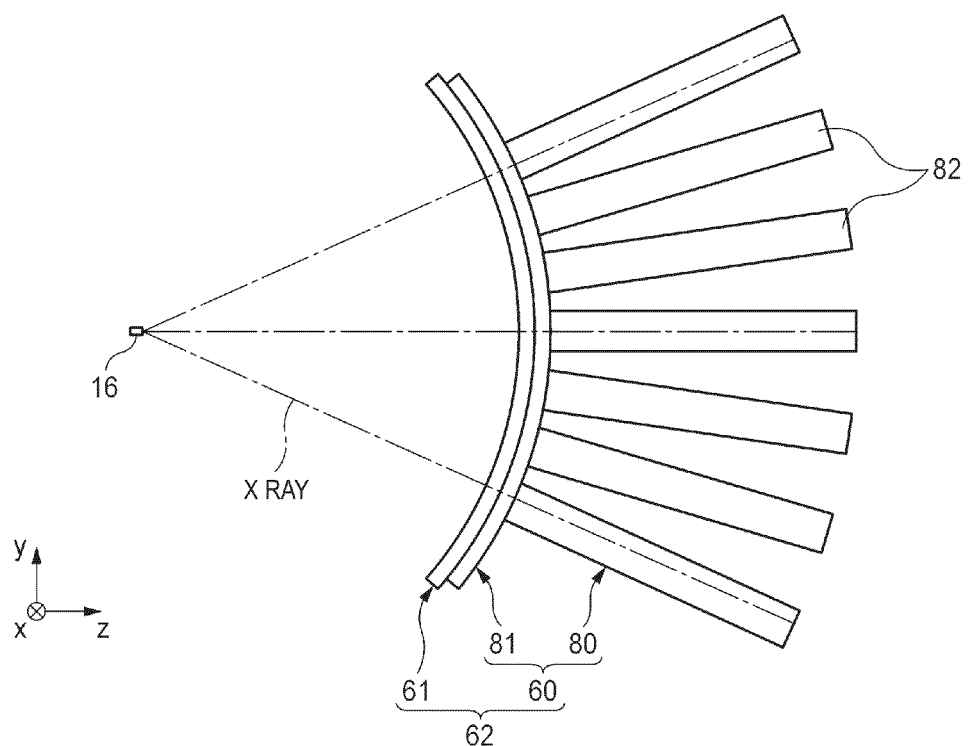
FIG. 12 is a view illustrating a state where the detection unit of the radiological image detection apparatus in FIG. 1 is curved.

FIG. 12 schematically illustrates the curved detection unit 62.

The respective columnar crystals 82 of the scintillator 60 exist independently of each other, as described above, with gaps around the columnar crystals 82. Even when the sensor panel 61 is curved, the gaps around the respective columnar crystals 82 are extended and retracted so that the columnar crystals 82 are kept perpendicular to the surface of the sensor panel 61. The sensor panel 61 is curved to conform to the substantially cylindrical surface around a center axis which is a straight line in parallel to the x direction passing through the X-ray focal point 16. Thus, the respective columnar crystals 82 are directed to the center axis and become substantially parallel to X-rays incident to the columnar crystals 82 from the plan view. This suppresses the X-rays from proceeding within the scintillator 60 through the plurality of columnar crystals 82, thereby improving the sharpness of an image.

In the detection unit 62 which is curved to locate the center of curvature at the X-ray incident plane side, the scintillator 60 is positioned at the outer diameter side, and along the curve of the detection unit 62, gaps between front end portions of the group of columnar crystals 82 are widened. Accordingly, front end portions of the adjacent columnar crystals 82 are avoided from coming in contact with each other, thereby suppressing the columnar crystals 82 from being damaged.

The non-columnar section 81 of the scintillator 60 which has a low porosity as compared to the columnar section 80 is adhered to the sensor panel 61 and the adhesion is increased. This suppresses the scintillator 60 from being peeled off due to the curve of the sensor panel 61.

In the above described X-ray image detection apparatus 3, the exposed detection unit 62 (the scintillator 60 and the sensor panel 61) is supported directly and curved by the support 63, in which the support 63 covers the detection unit 62 to shield light. However, as illustrated in FIG. 13, when the detection unit 62 is housed in a flexible case 100 having a light shielding property, the support 63 does not require the light shielding property.

Figure 13:
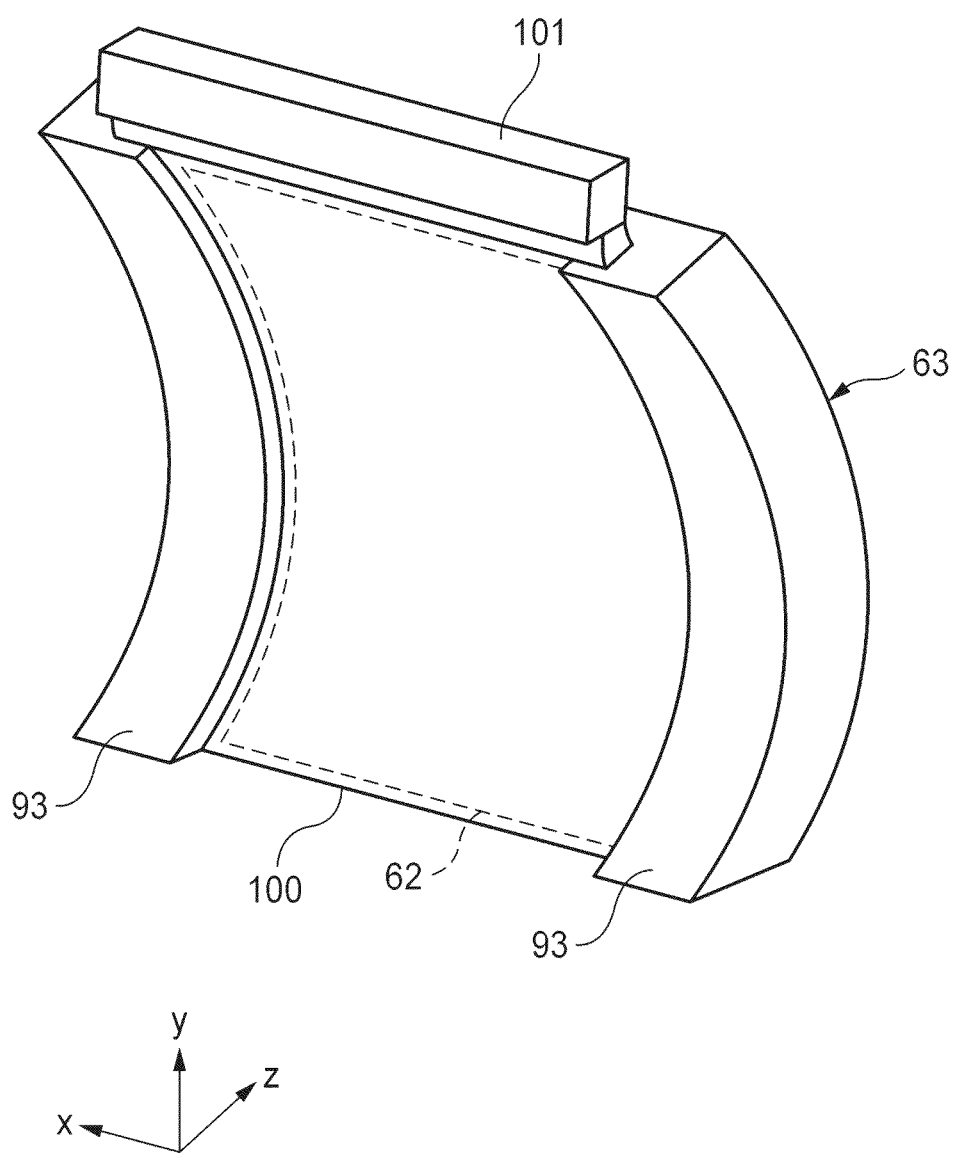
FIG. 13 is a view illustrating a modified example of the radiological image detection apparatus in FIG. 1.

In the example illustrated in FIG. 13, a control unit 101 that contains a circuit board which has a gate driver as an external circuit, and a signal processing unit is provided along one edge of the detection unit 62. To the circuit board, the gate lines 76 (see FIG. 4) or the signal lines 77 (see FIG. 4) are electrically connected. In the gate driver or the signal processing unit, a rigid IC which is typically made of an inorganic semiconductor material such as silicon is used, and thus it is difficult to curve the whole of the control unit containing them. In this case, it is preferable that one edge of the detection unit 62 mounted with the control unit 101 is disposed in parallel to the x direction, with respect to the support 63 which is curved to substantially conform to the cylindrical surface around a center axis which is a straight line in parallel to the x direction passing through the X-ray focal point 16, and only the detection unit 62 is supported by the support 63 to be curved.

Figure 14:
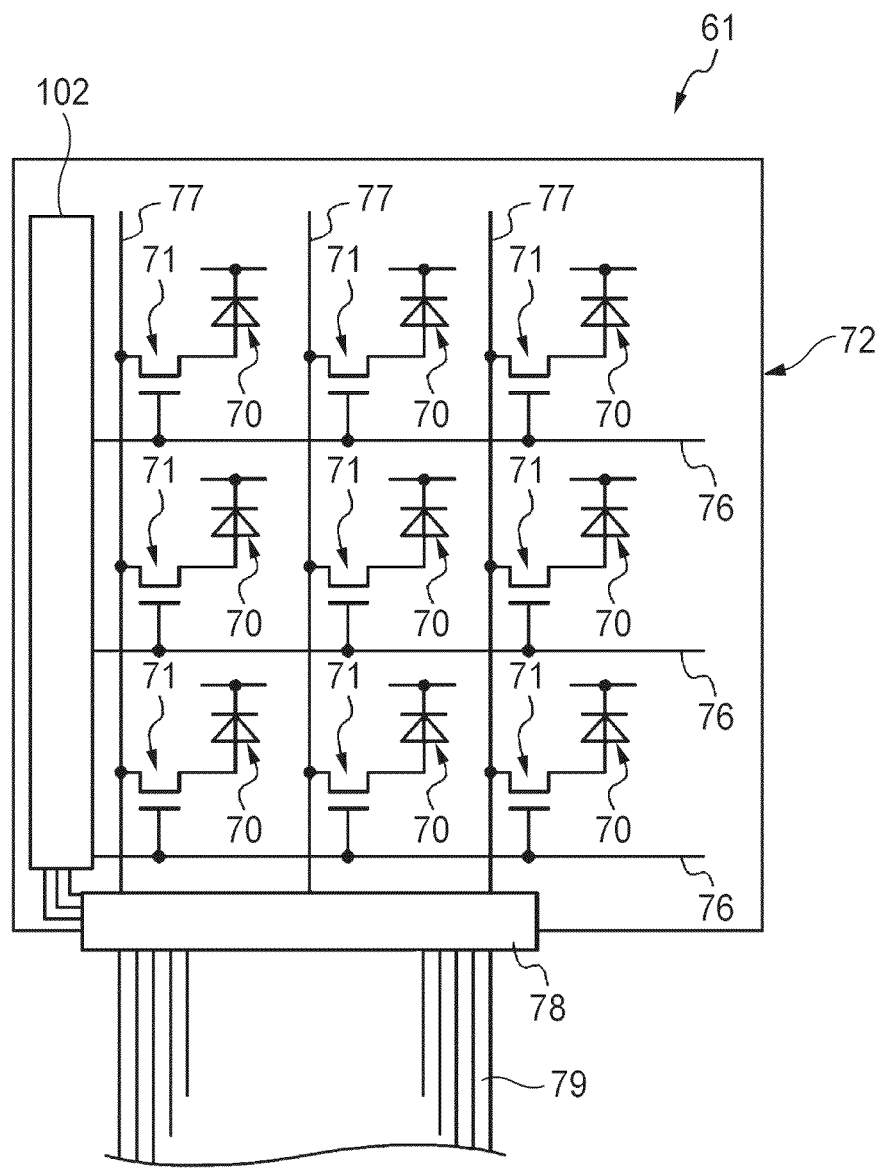
FIG. 14 is a view illustrating another modified example of the radiological image detection apparatus in FIG. 1.

In the gate driver, a gate driver circuit may be formed by a flexible organic TFT in place of the rigid IC made of the inorganic semiconductor material. Then, as illustrated in FIG. 14, a gate driver circuit 102 made of the organic TFT may be provided on the flexible TFT substrate 72 of the sensor panel 61. In this case, since the gate driver circuit 102 is flexible, the curve of the detection unit 62 is not suppressed.

In the above described X-ray image detection apparatus 3, as an example, the bimetal 90 is applied with an electric current, and is curved by self-heating. However, the temperature of the bimetal 90 may be controlled by a temperature control element such as a peltier element. Also, in the above description, as a driven member to be curved by heat as physical stimulation, the bimetal 90 is exemplarily used. However, a shape memory alloy may be used.

Figure 15:
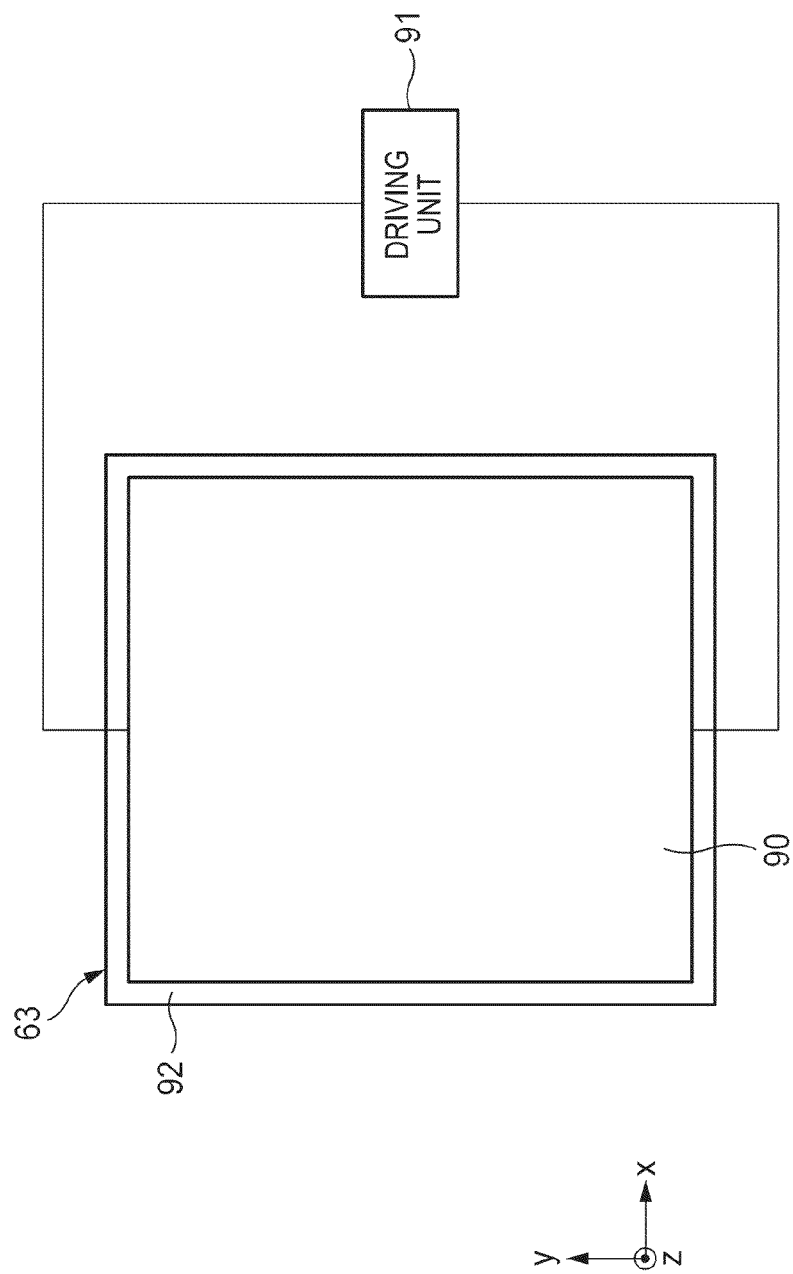
FIG. 15 is a view illustrating yet another modified example of the radiological image detection apparatus in FIG. 1.
Figure 16:
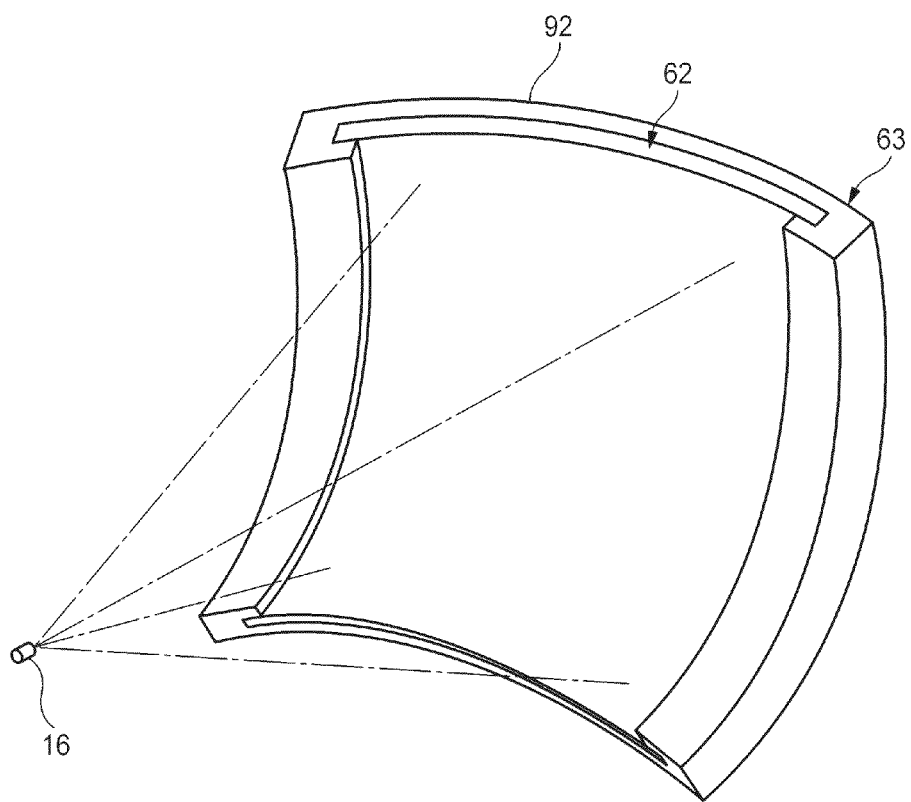
FIG. 16 is a view illustrating a state where a detection unit of the radiological image detection apparatus in FIG. 15 is curved.

FIGS. 15 and 16 illustrate yet another modified example of the above described X-ray image detection apparatus 3.

In an X-ray image detection apparatus 103 illustrated in FIGS. 15 and 16, one bimetal 90 is provided on the cover part 92 of the support 63 that supports the detection unit 62, which is formed in a size to cover almost the whole of the cover part 92. The bimetal 90 which is applied with an electric current from the driving unit 91 in accordance with an imaging distance SID set by the console 4 is curved to conform to the spherical surface around the X-ray focal point 16 as a center. In concurrence with curving the bimetal 90, the support 63, and the detection unit 62 supported by the support 63 are also curved to conform to the spherical surface around the X-ray focal point 16 as a center. Accordingly, the respective columnar crystals 82 are directed to the X-ray focal point 16, and become substantially parallel to X-rays incident to the columnar crystals 82. This suppresses the X-rays from proceeding within the scintillator 60 through the plurality of columnar crystals 82, thereby further improving the sharpness of an image.

Figure 17:
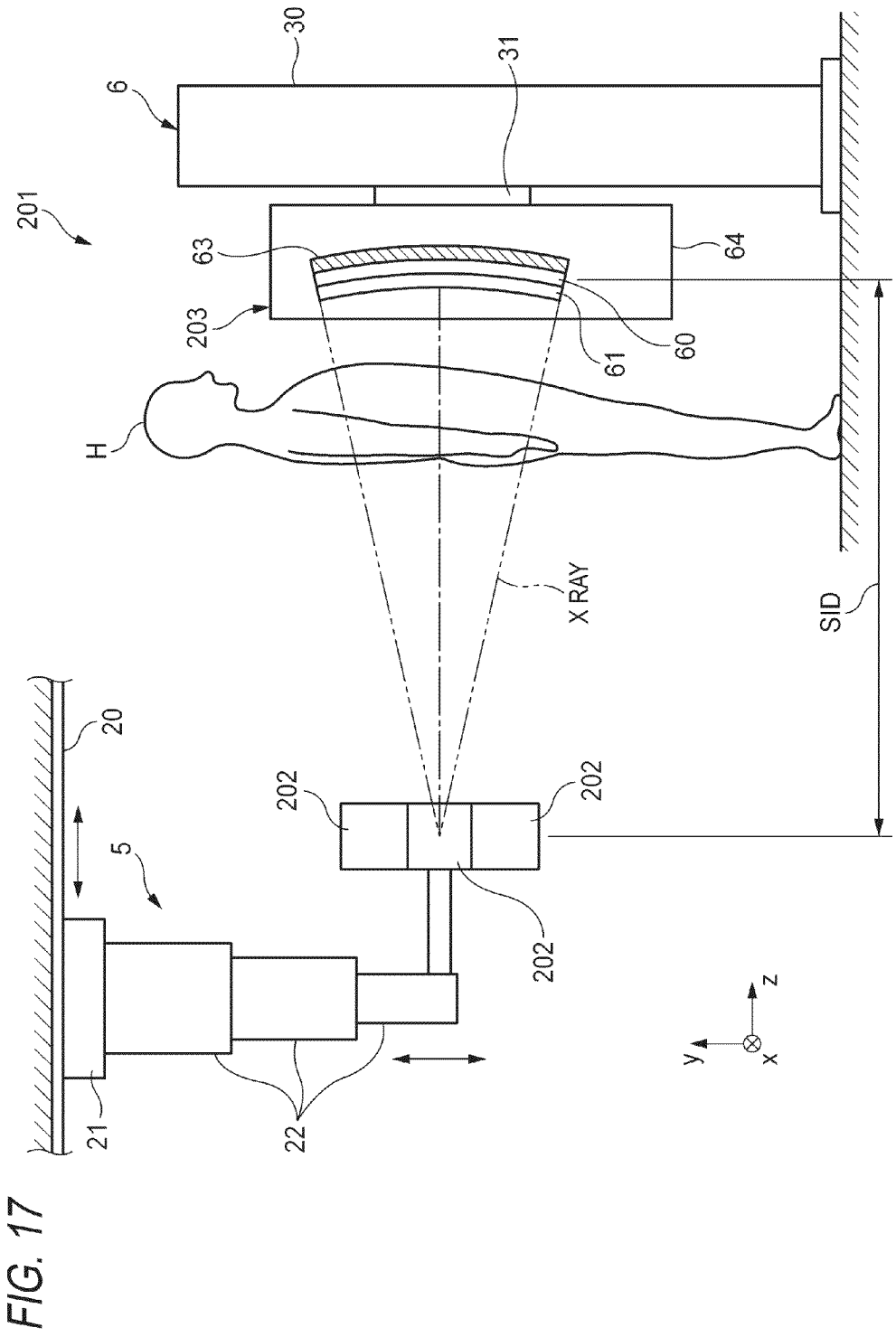
FIG. 17 is a view illustrating a modified example of the radiological image detection apparatus and the radiation imaging apparatus in FIG. 1.
Figure 18:
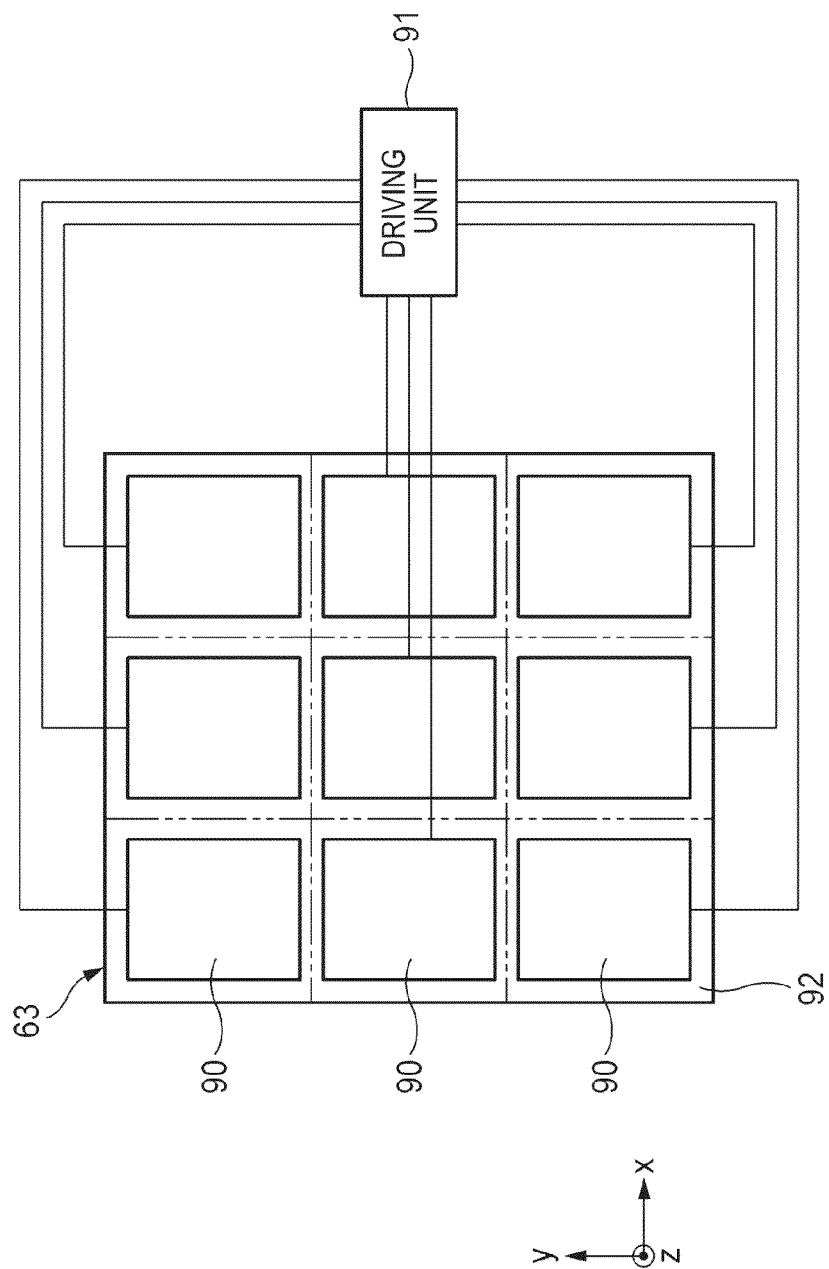
FIG. 18 is a view illustrating a configuration of a curving unit of the radiological image detection apparatus in FIG. 17.

FIG. 17 illustrates a modified example of the above described X-ray imaging apparatus 1, and FIG. 18 illustrates a configuration of an X-ray image detection apparatus of the X-ray imaging apparatus in FIG. 17.

An X-ray imaging apparatus 201 has a plurality of X-ray sources 202. X-rays are sequentially emitted from the X-ray sources 202 through the control by the control device 40 of the console 4, and an X-ray focal position is sequentially moved by switching the X-ray sources 202.

In an X-ray image detection apparatus 203, the cover part 92 of the support 63 that supports the detection unit 62 is divided into a plurality of regions, and bimetals 90 are provided in the respective regions. In the illustrated example, the cover part 92 is divided into three regions in each of the x direction and the y direction, and the respective regions are provided with the bimetals 90. The driving unit 91 is configured to control an electric current applied to the bimetals 90 independently of each other in accordance with the X-ray focal position.

FIGS. 19A to 19C schematically illustrate the curve of the detection unit 62 in the X-ray image detection apparatus 203.

Since the electric current which is controlled for the bimetals 90 independently of each other is applied from the driving unit 91, the radius of curvature of the detection unit 62, and the direction of a straight line which connects center of the detection unit 62 to center of curvature may be variously changed.

For example, when the electric currents applied to the bimetals 90 in the respective regions are the same, the detection unit 62 is curved in substantially symmetrical with the center of the detection unit 62. Here, the straight line which connects the center of the detection unit 62 to the corresponding curvature center is substantially along the z direction (FIG. 19A). When an electric current applied to the bimetal 90 in one side row region is set to be high and an electric current applied to the bimetal 90 in the other side row region is set to be low among electric currents applied to the bimetals 90 in the center row region in the y direction, the detection unit 62 is curved in asymmetrical with the center of the detection unit 62. Here, the straight line which connects the center of the detection unit 62 to the center of curvature is inclined with respect to the z direction (FIGS. 19B, and 19C).

As described above, by controlling the electric current applied to the bimetals 90 independently of each other in accordance with the X-ray focal position, the curvature center of the detection unit 62 may conform to the X-ray focal position that is sequentially moved by switching the X-ray sources 202. Accordingly, with respect to radiation emitted from different X-ray focal positions, the respective columnar crystals 82 of the scintillator 60 may be substantially parallel to X-rays incident to the columnar crystals 82.

Figure 20:
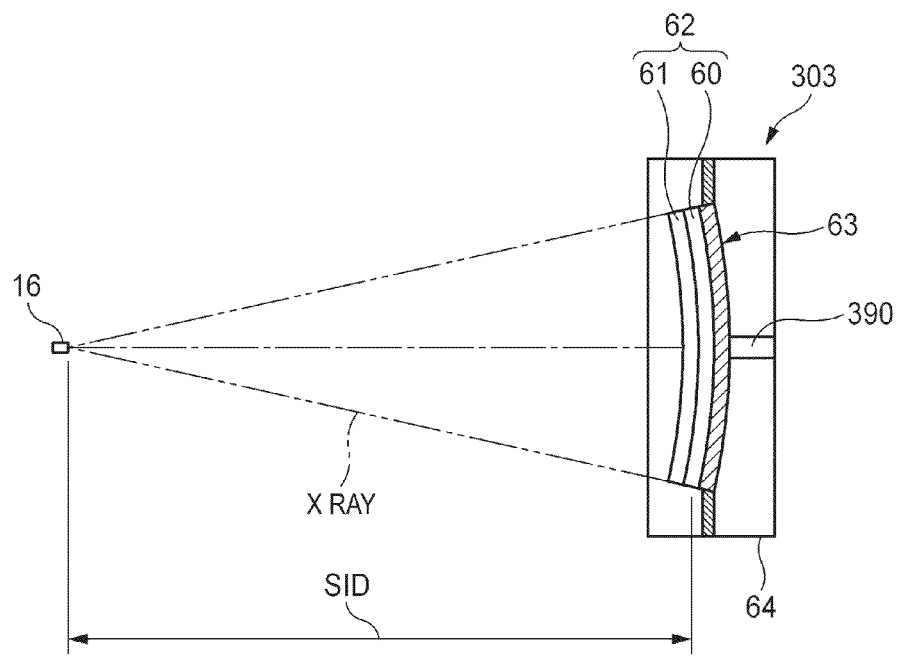
FIG. 20 is a view illustrating still another modified example of the radiological image detection apparatus in FIG. 1.

FIG. 20 illustrates still another modified example of the above described X-ray image detection apparatus 3.

In the above described X-ray image detection apparatus 3 and modified examples thereof, as a driven member configured to curve the detection unit 62, for example, the bimetal to be curved by heat as external stimulation is exemplarily used. However, a driven member which is extended or retracted by external stimulation may be used, and as for such a driven member, for example, a piezoelectric element or an artificial muscle which uses volume phase transition of polymer gel may be exemplified. These are extended or retracted by applied voltage as external stimulation.

In an X-ray image detection apparatus 303 illustrated in FIG. 20, the outer periphery of the support 63 that supports the detection unit 62 is fixed to the inner wall of the case 64. An artificial muscle 390 is provided at the center of the cover part 92 of the support 63.

One end in the extension/retraction direction of the artificial muscle 390 is connected to the support 63, and the other end is fixed to the inner wall of the case 64 opposed to the support 63. A driving unit (not illustrated) is configured to control a voltage applied to the artificial muscle 390 in accordance with an imaging distance SID. When the artificial muscle 390 applied with the voltage from the driving unit 91 in accordance with the imaging distance SID is retracted, the support 63 is curved to conform to the spherical surface around the X-ray focal point 16 as the center, and the detection unit 62 supported by the support 63 is also curved to conform to the spherical surface around the X-ray focal point 16 as the center. Accordingly, the respective columnar crystals 82 are directed to the X-ray focal point 16, and become substantially parallel to X-rays incident to the columnar crystals 82.

In another configuration, the center of the cover part 92 of the support 63 may be fixed to the case 64 so that the outer periphery of the support 63 may be supported by a plurality of artificial muscles 390. In the configuration, a voltage applied to the respective artificial muscles 390 may be controlled for the artificial muscles 390 independently of each other. Here, in the same manner as the X-ray image detection apparatus 203 in the above described X-ray imaging apparatus 201, by controlling the voltage applied to the respective artificial muscles 390 independently of each other in accordance with the X-ray focal position, the curvature center of the detection unit 62 may conform to the X-ray focal position that is sequentially moved by switching the X-ray sources 202.

Each of the above described radiological image detection apparatus may detect a radiological image with a high sensitivity and a high definition, and thus may be used while embedded within various devices requiring detection of a sharp image at a low radiation irradiation dose, including an X-ray imaging device for medical diagnosis such as mammography. For example, the device has a wide application range thereof because it may be used as an X-ray imaging device for industrial use for a non-destructive test, or as a device for detecting corpuscular beams (α rays, β-rays, γ rays) besides electromagnetic waves.

Hereinafter, materials that may be used for respective components constituting the sensor panel 61 will be described.

[Photoelectric Conversion Element]

Although inorganic semiconductor materials such as amorphous silicon are often used as the photoconductive layers 73 of the aforementioned photoelectric conversion elements 70 (refer to FIG. 3), any OPC (Organic Photoelectric Conversion) material disclosed in JPA-2009-32854 can be used. A film formed out of the OPC material (hereinafter referred to as OPC film) can be used as the photoconductive layers 73. The OPC film contains an organic photoelectric conversion material, which absorbs light emitted from the scintillator and generates electric charges corresponding to the absorbed light. Thus, the OPC film containing the organic photoelectric conversion material has a sharp absorption spectrum in a visible light range. Electromagnetic waves other than the light emitted by the scintillator are hardly absorbed by the OPC film. Thus, noise generated by radioactive rays such as X-rays absorbed by the OPC film can be suppressed effectively.

It is preferable that the absorption peak wavelength of the organic photoelectric conversion material forming the OPC film is closer to the peak wavelength of light emitted by the scintillator in order to more efficiently absorb the light emitted by the scintillator. Ideally, the absorption peak wavelength of the organic photoelectric conversion material agrees with the peak wavelength of the light emitted by the scintillator. However, if the difference between the absorption peak wavelength of the organic photoelectric conversion material and the peak wavelength of the light emitted by the scintillator is small, the light emitted by the scintillator can be absorbed satisfactorily. Specifically, the difference between the absorption peak wavelength of the organic photoelectric conversion material and the peak wavelength of the light emitted by the scintillator in response to radioactive rays is preferably not larger than 10 nm, more preferably not larger than 5 nm.

Examples of the organic photoelectric conversion material that can satisfy such conditions include arylidene-based organic compounds, quinacridone-based organic compounds, and phthalocyanine-based organic compounds. For example, the absorption peak wavelength of quinacridone in a visible light range is 560 nm. Therefore, when quinacridone is used as the organic photoelectric conversion material and CsI(Tl) is used as the scintillator material, the aforementioned difference in peak wavelength can be set within 5 nm so that the amount of electric charges generated in the OPC film can be increased substantially to the maximum.

At least a part of an organic layer provided between the bias electrode 74a and the charge collection electrode 74b can be formed out of an OPC film. More specifically, the organic layer can be formed out of a stack or a mixture of a portion for absorbing electromagnetic waves, a photoelectric conversion portion, an electron transport portion, an electron hole transport portion, an electron blocking portion, an electron hole blocking portion, a crystallization prevention portion, electrodes, interlayer contact improvement portions, etc.

Preferably the organic layer contains an organic p-type compound or an organic n-type compound. An organic p-type semiconductor (compound) is a donor-type organic semiconductor (compound) as chiefly represented by an electron hole transport organic compound, meaning an organic compound having characteristic to easily donate electrons. More in detail, of two organic materials used in contact with each other, one with lower ionization potential is called the donor-type organic compound. Therefore, any organic compound may be used as the donor-type organic compound as long as the organic compound having characteristic to donate electrons. Examples of the donor-type organic compound that can be used include a triarylamine compound, a benzidine compound, a pyrazoline compound, a styrylamine compound, a hydrazone compound, a triphenylmethane compound, a carbazole compound, a polysilane compound, a thiophene compound, a phthalocyanine compound, a cyanine compound, a merocyanine compound, an oxonol compound, a polyamine compound, an indole compound, a pyrrole compound, a pyrazole compound, a polyarylene compound, a fused aromatic carbocyclic compound (naphthalene derivative, anthracene derivative, phenanthrene derivative, tetracene derivative, pyrene derivative, perylene derivative, fluoranthene derivative), a metal complex having a nitrogen-containing heterocyclic compound as a ligand, etc. The donor-type organic semiconductor is not limited thereto but any organic compound having lower ionization potential than the organic compound used as an n-type (acceptor-type) compound may be used as the donor-type organic semiconductor.

The n-type organic semiconductor (compound) is an acceptor-type organic semiconductor (compound) as chiefly represented by an electron transport organic compound, meaning an organic compound having characteristic to easily accept electrons. More specifically, when two organic compounds are used in contact with each other, one of the two organic compounds with higher electron affinity is the acceptor-type organic compound. Therefore, any organic compound may be used as the acceptor-type organic compound as long as the organic compound having characteristic to accept electrons. Examples thereof include a fused aromatic carbocyclic compound (naphthalene derivative, anthracene derivative, phenanthrene derivative, tetracene derivative, pyrene derivative, perylene derivative, fluoranthene derivative), a 5- to 7-membered heterocyclic compound containing a nitrogen atom, an oxygen atom or a sulfur atom (e.g. pyridine, pyrazine, pyrimidine, pyridazine, triazine, quinoline, quinoxaline, quinazoline, phthalazine, cinnoline, isoquinoline, pteridine, acridine, phenazine, phenanthroline, tetrazole, pyrazole, imidazole, thiazole, oxazole, indazole, benzimidazole, benzotriazole, benzoxazole, benzothiazole, carbazole, purine, triazolopyridazine, triazolopyrimidine, tetrazaindene, oxadiazole, imidazopyridine, pyralidine, pyrrolopyridine, thiadiazolopyridine, dibenzazepine, tribenzazepine etc.), a polyarylene compound, a fluorene compound, a cyclopentadiene compound, a silyl compound, and a metal complex having a nitrogen-containing heterocyclic compound as a ligand. The acceptor-type organic semiconductor is not limited thereto. Any organic compound may be used as the acceptor-type organic semiconductor as long as the organic compound has higher electron affinity than the organic compound used as the donor-type organic compound.

As for p-type organic dye or n-type organic dye, any known dye may be used. Preferred examples thereof include cyanine dyes, styryl dyes, hemicyanine dyes, merocyanine dyes (including zero-methine merocyanine (simple merocyanine)), trinuclear merocyanine dyes, tetranuclear merocyanine dyes, rhodacyanine dyes, complex cyanine dyes, complex merocyanine dyes, alopolar dyes, oxonol dyes, hemioxonol dyes, squarylium dyes, croconium dyes, azamethine dyes, coumarin dyes, arylidene dyes, anthraquinone dyes, triphenylmethane dyes, azo dyes, azomethine dyes, spiro compounds, metallocene dyes, fluorenone dyes, flugide dyes, perylene dyes, phenazine dyes, phenothiazine dyes, quinone dyes, indigo dyes, diphenylmethane dyes, polyene dyes, acridine dyes, acridinone dyes, diphenylamine dyes, quinacridone dyes, quinophthalone dyes, phenoxazine dyes, phthaloperylene dyes, porphyrin dyes, chlorophyll dyes, phthalocyanine dyes, metal complex dyes, and fused aromatic carbocyclic dyes (naphthalene derivative, anthracene derivative, phenanthrene derivative, tetracene derivative, pyrene derivative, perylene derivative, fluoranthene derivative).

A photoelectric conversion film (photosensitive layer) which has a layer of a p-type semiconductor and a layer of an n-type semiconductor between a pair of electrodes and at least one of the p-type semiconductor and the n-type semiconductor is an organic semiconductor and in which a bulk heterojunction structure layer including the p-type semiconductor and the n-type semiconductor is provided as an intermediate layer between those semiconductor layers may be used preferably. The bulk heterojunction structure layer included in the photoelectric conversion film can cover the defect that the carrier diffusion length of the organic layer is short. Thus, the photoelectric conversion efficiency can be improved. The bulk heterojunction structure has been described in detail in JP-A-2005-303266.

It is preferable that the photoelectric conversion film is thicker in view of absorption of light from the phosphor layer. The photoelectric conversion film is preferably not thinner than 30 nm and not thicker than 300 nm, more preferably not thinner than 50 nm and not thicker than 250 nm, particularly more preferably not thinner than 80 nm and not thicker than 200 nm in consideration of the ratio which does make any contribution to separation of electric charges.

As for any other configuration about the aforementioned OPC film, for example, refer to description in JP-A-2009-32854.

[Switching Device]

Although inorganic semiconductor materials such as amorphous silicon are often used as an active layer of the switching devices 71, organic materials may be used, for example, as disclosed in JP-A-2009-212389. Organic TFT may have any type of structure but a field effect transistor (FET) structure is the most preferable. In the FET structure, a gate electrode is provided partially an upper surface of an insulation substrate. An insulator layer is provided to cover the electrode and touch the substrate in the other portion than the electrode. Further, a semiconductor active layer is provided on an upper surface of the insulator layer, and a transparent source electrode and a transparent drain electrode are disposed partially on the upper surface of the semiconductor active layer and at a distance from each other. This configuration is called a top contact type device. A bottom contact type device in which a source electrode and a drain electrode are disposed under a semiconductor active layer may be also used preferably. In addition, a vertical transistor structure in which a carrier flows in the thickness direction of an organic semiconductor film may be used.

(Active Layer)

Organic semiconductor materials mentioned herein are organic materials showing properties as semiconductors. Examples of the organic semiconductor materials include p-type organic semiconductor materials (or referred to as p-type materials simply or as electron hole transport materials) which conduct electron holes (holes) as carriers, and n-type organic semiconductor materials (or referred to as n-type materials simply or as electrode transport materials) which conduct electrons as carriers, similarly to a semiconductor formed out of an inorganic material. Of the organic semiconductor materials, lots of p-type materials generally show good properties. In addition, p-type transistors are generally excellent in operating stability as transistors under the atmosphere. Here, description here will be made on a p-type organic semiconductor material.

One of properties of organic thin film transistors is a carrier mobility (also referred to as mobility simply) μ which indicates the mobility of a carrier in an organic semiconductor layer. Although preferred mobility varies in accordance with applications, higher mobility is generally preferred. The mobility is preferably not lower than $1.0 \times 10^{-7}$ cm$^2$/Vs, more preferably not lower than $1.0 \times 10^{-6}$ cm$^2$/Vs, further preferably not lower than $1.0 \times 10^{-5}$ cm$^2$/Vs. The mobility can be obtained by properties or TOF (Time Of Flight) measurement when the field effect transistor (FET) device is manufactured.

The p-type organic semiconductor material may be either a low molecular weight material or a high molecular weight material, but preferably a low molecular weight material. Lots of low molecular weight materials typically show excellent properties due to easiness in high purification because various refining processes such as sublimation refining, recrystallization, column chromatography, etc. can be applied thereto, or due to easiness in formation of a highly ordered crystal structure because the low molecular weight materials have a fixed molecular structure. The molecular weight of the low molecular weight material is preferably not lower than 100 and not higher than 5,000, more preferably not lower than 150 and not higher than 3,000, further more preferably not lower than 200 and not higher than 2,000.

As for such a p-type organic semiconductor material, a phthalocyanine compound or a naphthalocyanine compound may be exemplarily used. Specific examples thereof are noted below. Also, M represents a metal atom, Bu represents a butyl group, Pr represents a propyl group, Et represents an ethyl group, and Ph represents a phenyl group.

[Chem 1]

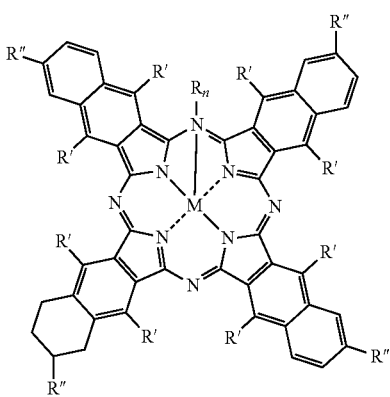

Compound 1 to 15

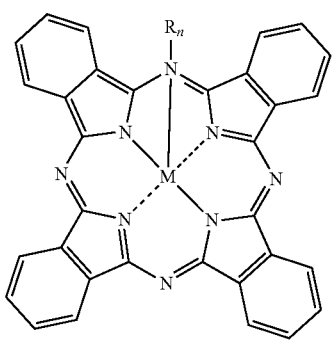

Compound 16 to 20

| Compound | M | R | n | R' | R" |
|---|---|---|---|---|---|
| 1 | Si | OSi(n-Bu)$_3$ | 2 | H | H |
| 2 | Si | OSi(i-Pr)$_3$ | 2 | H | H |
| 3 | Si | OSi(OEt)$_3$ | 2 | H | H |
| 4 | Si | OSiPh$_3$ | 2 | H | H |
| 5 | Si | O(n-C$_8$H$_{17}$) | 2 | H | H |
| 7 | Ge | OSi(n-Bu)$_3$ | 2 | H | H |
| 8 | Sn | OSi(n-Bu)$_3$ | 2 | H | H |
| 9 | Al | OSi(n-C$_6$H$_{13}$)$_3$ | 1 | H | H |
| 10 | Ga | OSi(n-C$_6$H$_{13}$)$_3$ | 1 | H | H |
| 11 | Cu | — | — | O(n-Bu) | H |
| 12 | Ni | — | — | O(n-Bu) | H |
| 13 | Zn | — | — | H | t-Bu |
| 14 | V=O | — | — | H | t-Bu |
| 15 | H$_2$ | — | — | H | t-Bu |
| 16 | Si | OSiEt$_3$ | 2 | — | — |
| 17 | Ge | OSiEt$_3$ | 2 | — | — |
| 18 | Sn | OSiEt$_3$ | 2 | — | — |
| 19 | Al | OSiEt$_3$ | 1 | — | — |
| 20 | Ga | OSiEt$_3$ | 1 | — | — |

(Switching Device Constituent Components Other than the Active Layer)

There is no particular limitation in the material constituting the gate electrode, the source electrode, or the drain electrode, as long as it has a required conductivity. However, examples thereof may include a transparent conductive oxide such as ITO (indium-doped tin oxide), IZO (indium-doped zinc oxide), SnO$_2$, ATO (antimony-doped tin oxide), ZnO, AZO (aluminum-doped zinc oxide), GZO (gallium-doped zinc oxide), TiO$_2$, or FTO (fluorine-doped tin oxide), a transparent conductive polymer such as PEDOT/PSS ([poly(3,4-ethylenedioxythiophene)/polystyrene sulfonic acid), or a carbon material such as carbon nanotube. These electrode materials may be film-formed by, for example, a vacuum evaporation method, a sputtering method, or a solution coating method.

There is no particular limitation in the material used for the insulating layer, as long as it has a required insulating effect. Examples thereof may include an inorganic material such as silicon dioxide, silicon nitride, or alumina, or an organic material such as polyester (e.g., PEN (polyethylene naphthalate), PET (polyethylene terephthalate)), polycarbonate, polyimide, polyamide, polyacrylate, epoxy resin, poly-para-xylylene resin, novolac resin, PVA (polyvinyl alcohol), PS (polystyrene). These insulating film materials may be film-formed by, for example, a vacuum evaporation method, a sputtering method, or a solution coating method.

Other configurations on the above described organic TFT may refer to the description of JP-A-2009-212389.

Also, in the active layer of the switching devices 71, for example, an amorphous oxide described in JP-A-2010-186860 may be used. Hereinafter, an active layer containing the amorphous oxide included in a field effect transistor (FET) described in JP-A-2010-186860 will be described. The active layer serves as a channel layer of the FET, allowing electrons or holes to move.

The active layer is configured to include an amorphous oxide semiconductor. The amorphous oxide semiconductor may be film-formed at a low temperature, and thus may be appropriately formed on a flexible substrate. The amorphous oxide semiconductor used in the active layer may be preferably an amorphous oxide that includes at least one kind element selected from the group including In, Sn, Zn, and Cd, more preferably an amorphous oxide that includes at least one kind selected from the group including In, Sn, and Zn, and further more preferably, an amorphous oxide that includes at least one kind selected from the group including In, and Zn.

Examples of the amorphous oxide used in the active layer, specifically, may include In$_2$O$_3$, ZnO, SnO$_2$, CdO, Indium-Zinc-Oxide (IZO), Indium-Tin-Oxide (ITO), Gallium-Zinc-Oxide (GZO), Indium-Gallium-Oxide (IGO), or Indium-Gallium-Zinc-Oxide (IGZO).

As for the film forming method of the active layer, a vapor-phase film formation method may be preferably used with a polycrystalline sintered body of the oxide semiconductor as a target. Among vapor-phase film formation methods, a sputtering method, or a pulsed laser deposition method (PLD method) is suitable. Further, from the view point of mass production, the sputtering method is preferable. For example, the film formation may be performed by an RF magnetron sputtering evaporation method while the degree of vacuum and the oxygen flow rate are controlled.

The film-formed active layer is determined to be an amorphous film, through a known X-ray diffraction method. The composition ratio of the active layer may be obtained by an RBS (Rutherford Back Scattering) analysis method.

Further, the electrical conductivity of the active layer is preferably $10^{-4}$ Scm$^{-1}$ or more and less than $10^2$ Scm$^{-1}$, and more preferably $10^{-1}$ Scm$^{-1}$ or more and less than $10^2$ Scm$^{-1}$. A method of adjusting the electrical conductivity of the active layer may include known methods such as an adjustment method according to oxygen defects, an adjustment method according to a composition ratio, an adjustment method according to impurities, and an adjustment method according to an oxide semiconductor material.

Other configurations on the above amorphous oxide may refer to the description of JP-A-2010-186860.

[Flexible Insulating Substrate]

The flexible substrate is not limited particularly as long as it has required smoothness. Examples of the substrate include light transmissive plastic film, etc. Examples of the light transmissive plastic film include films or the like, made from polyethylene terephthalate (PET), polyethylene naphthalate (PEN), polyether sulfone (PES), polyether imide, polyetheretherketone, polyphenylene sulfide, polyalylate, polyimide, polycarbonate (PC), cellulose triacetate (TAC), cellulose acetate propionate (CAP), etc. In addition, any organic or inorganic filler may be contained in these plastic films. It may be considered that aramid, bionanofiber, etc. having properties such as flexibility, low thermal expansion and high strength, which cannot be obtained in existing glass or plastic, are used preferably to form a flexible substrate.

(Aramid)

An aramid material has high heat resistance showing a glass transition temperature of 315° C., high rigidity showing a Young's modulus of 10 GPa, and high dimensional stability showing a thermal expansion coefficient of −3 to 5 ppm/° C. Therefore, when a film made from aramid is used, it is possible to easily form a high-quality film for a semiconductor layer, as compared with the case where a general resin film is used. In addition, due to the high heat resistance of the aramid material, an electrode material can be cured at a high temperature to have low resistance. Further, it is also possible to deal with automatic mounting with ICs, including a solder reflow step. Furthermore, since the aramid material has a thermal expansion coefficient close to that of ITO (indium tin oxide), a gas barrier film or a glass substrate, warp after manufacturing is small. In addition, cracking hardly occurs. Here, it is preferable to use a halogen-free (in conformity with the requirements of JPCA-ES01-2003) aramid material containing no halogens, in view of reduction of environmental load.

The aramid film may be laminated with a glass substrate or a PET substrate, or may be pasted onto a housing of a device.

High intermolecular cohesion (hydrogen bonding force) of aramid leads to low solubility to a solvent. When the problem of the low solubility is solved by molecular design, an aramid material easily formed into a colorless and transparent thin film can be used preferably. Due to molecular design for controlling the order of monomer units and the substituent species and position on an aromatic ring, easy formation with good solubility can be obtained with the molecular structure kept in a bar-like shape with high linearity leading to high rigidity or dimensional stability of the aramid material. Due to the molecular design, halogen-free can be also achieved.

In addition, an aramid material having an optimized characteristic in an in-plane direction of a film can be used preferably. Tensional conditions are controlled in each step of solution casting, vertical drawing and horizontal drawing in accordance with the strength of the aramid film which varies constantly during casting. Due to the control of the tensional conditions, the in-plane characteristic of the aramid film which has a bar-like molecular structure with high linearity leading to easy occurrence of anisotropic physicality can be balanced.

Specifically, in the solution casting step, the drying rate of the solvent is controlled to make the in-plane thickness-direction physicality isotropic and optimize the strength of the film including the solvent and the peel strength from a casting drum. In the vertical drawing step, the drawing conditions are controlled precisely in accordance with the film strength varying constantly during drawing and the residual amount of the solvent. In the horizontal drawing, the horizontal drawing conditions are controlled in accordance with a change in film strength varying due to heating and controlled to relax the residual stress of the film. By use of such an aramid material, the problem that the aramid film after casting may be curled.

In each of the contrivance for the easiness of casting and the contrivance for the balance of the film in-plane characteristic, the bar-like molecular structure with high linearity peculiar to aramid can be kept to keep the thermal expansion coefficient low. When the drawing conditions during film formation are changed, the thermal expansion coefficient can be reduced further.

(Bio-Nanofiber)

Components sufficiently small relative to the wavelength of light produce no scattering of the light. Accordingly, nanofibers may be used as a support for a transparent flexible resin material. And, of the nanofibers, a composite material (occasionally referred to as bionanofiber) of bacterial cellulose and transparent resin can be used preferably. The bacterial cellulose is produced by bacteria (*Acetobacter Xylinum*). The bacterial cellulose has a cellulose microfibril bundle width of 50 nm, which is about 1/10 as large as the wavelength of visible light. In addition, the bacterial cellulose is characterized by high strength, high elasticity and low thermal expansion.

When a bacterial cellulose sheet is impregnated with transparent resin such as acrylic resin or epoxy resin and hardened, transparent bionanofiber showing a light transmittance of about 90% in a wavelength of 500 nm while having a high fiber ratio of about 60 to 70% can be obtained. By the bionanofiber, a thermal expansion coefficient (about 3 to 7 ppm) as low as that of silicon crystal, strength (about 460 MPa) as high as that of steel, and high elasticity (about 30 GPa) can be obtained.

As for the configuration about the aforementioned bionanofiber, for example, refer to description in JP-A-2008-34556.

By impregnating a bacteria cellulose sheet with a transparent resin such as an acrylic resin or an epoxy resin and curing the transparent resin, a transparent bionanofiber which contains fibers in a high ratio of about 60 to 70% and inhibits light transmittance of about 90% at a wavelength of 500 nm may be obtained. By the bionanofiber, a low thermal expansion coefficient (about 3 to 7 ppm) comparable to that of a silicon crystal, a strength (about 460 MPa) on the same level as steel, and a high modulus (about 30 GPa) may be achieved.

For the above described configuration of the bionanofiber, see, for example, JP-A-2008-34556.

As described above, the present description discloses the following radiological image detection apparatuses (1) to (13).

(1) A radiological image detection apparatus includes: a phosphor which contains a fluorescent material that emits fluorescence by radiation exposure, and a sensor panel which is provided to be in close contact with the phosphor, and detects the fluorescence emitted from the phosphor, in which the phosphor includes a columnar section that is formed by a group of columnar crystals formed by growing crystals of the fluorescent material in a columnar shape, a radiation incident plane is provided in the sensor panel at a side opposite to the phosphor, and the sensor panel has flexibility and is curved to locate a curvature center at the side of the radiation incident plane.

(2) The radiological image detection apparatus of (1), may further include a curving unit configured to support the sensor panel and to curve the sensor panel such that a position of the curvature center is variable.

(3) In the radiological image detection apparatus of (2), the curving unit curves the sensor panel such that the radius of curvature of the sensor panel is variable.

(4) In the radiological image detection apparatus of (2) or (3), the curving unit curves the sensor panel such that a direction of a straight line which connects a center of the sensor panel to the curvature center is variable.

(5) In the radiological image detection apparatus of any one of (2) to (4), the curving unit includes at least one driven member which is curved by physical stimulation and affixed to the sensor panel.

(6) In the radiological image detection apparatus of (5), the driven member is a bimetal.

(7) In the radiological image detection apparatus of (6), the curving unit has a driving unit configured to apply an electric current to the bimetal.

(8) In the radiological image detection apparatus of any one of (2) to (4), the curving unit includes at least one driven member which is extended or retracted by physical stimulation, and has one end connected to the sensor panel, and another end which is fixed.

(9) In the radiological image detection apparatus of any one of (5) to (8), the curving unit has a plurality of the driven members, and applies the physical stimulation to the driven members independently of each other.

(10) In the radiological image detection apparatus of any one of (5) to (9), the curving unit has a support configured to support the sensor panel, the support includes a cover part configured to cover a surface opposite to a surface of the sensor panel which is in close contact with the phosphor, and an engaging part configured to engage an edge of the sensor panel, and the driven member is provided on the cover part.

(11) In the radiological image detection apparatus of (10), the support has flexibility.

(12) In the radiological image detection apparatus of any one of (1) to (11), the phosphor further includes a non-columnar section that has a low porosity as compared to the columnar section, and the non-columnar section is in close contact with the sensor panel.

(13) In the radiological image detection apparatus of (12), the non-columnar section has a thickness ranging from 5 μm to 50 μm.

As described above, the present description discloses the following radiological image detection apparatuses (14) and (15).

(14) A radiation imaging apparatus includes: the radiological image detection apparatus of any one of (1) to (13); and a radiation source configured to irradiate radiation toward the radiological image detection apparatus, in which the curvature center of the sensor panel corresponds to a focal point of the radiation source.

(15) A radiation imaging apparatus includes: the radiological image detection apparatus of any one of (2) to (9); a radiation source configured to irradiate radiation toward the radiological image detection apparatus; and a detection unit configured to detect a relative position of the radiation source with respect to the radiological image detection apparatus, in which the curving unit curves the sensor panel such that a position of the curvature center of the sensor panel is variable in accordance with the relative position of the radiation source which is detected by the detection unit.

INDUSTRIAL APPLICABILITY

According to the present invention, with respect to the sensor panel that is curved to locate the center of curvature at radiation incident plane side, the phosphor is disposed at the outer diameter side, and gaps between front end portions of the group of columnar crystals constituting the phosphor are widened. Accordingly, front end portions of the adjacent columnar crystals are avoided from coming in contact with each other, thereby suppressing the columnar crystals from being damaged. Thus, even if an imaging distance is relatively short, the respective columnar crystals may be disposed to be parallel to radiation in accordance with the imaging distance, thereby improving the sharpness of an image.

The present invention has been described in detail with reference to specific exemplary embodiments, but it is apparent to the person skilled in the art that various modifications or changes may be made without departing from the scope and spirit of the present invention.

This application is based on Japanese Patent Application No. 2011-035227, filed on Feb. 21, 2011, the disclosure of which is incorporated herein in its entirety by reference.

REFERENCE SIGNS LIST

1 X ray-imaging system
2 X-ray source
3 X-ray image detection apparatus
4 console
5 X-ray source holding device
6 stand
10 X-ray source control unit
11 high voltage generator
12 X-ray tube
13 collimator
14 collimator unit
15 rotary anode
16 X-ray focal point
20 ceiling rail
21 carriage unit
22 strut
30 main body
31 holding part
40 control device
41 input device
42 image processing unit
43 storage unit
44 monitor
46 bus
60 scintillator
61 sensor panel
62 detection unit
63 support
64 case
65 curving unit
70 photoelectric conversion element
71 switching device
72 flexible TFT substrate
73 photoconductive layer
74a bias electrode
74b charge collection electrode
75 flattening layer
76 gate line
77 signal line
78 connection terminal
79 connection circuit
80 columnar section
81 non-columnar section
82 columnar crystal
83 substrate
90 bimetal (driven member)
91 driving unit
92 cover part
93 engaging part

The invention claimed is:
1. A radiological image detection apparatus comprising:
a phosphor which contains a fluorescent material that emits fluorescence by radiation exposure; and a sensor panel which is provided to be in close contact with the phosphor, and detects the fluorescence emitted from the phosphor, wherein the phosphor includes a columnar section that is formed by a group of columnar crystals formed by growing crystals of the fluorescent material in a columnar shape, one ends of the columnar crystals in a growing direction of the columnar crystals are attached to the sensor panel and distances between the other ends of the columnar crystals are capable of being enlarged and reduced, a radiation incident plane is provided in the sensor panel at a side opposite to the phosphor, and the sensor panel has flexibility and is curved to locate a curvature center at the side of the radiation incident plane.

2. The radiological image detection apparatus of claim 1, further comprising a curving unit configured to support the sensor panel and to curve the sensor panel such that a position of the curvature center is variable.

3. The radiological image detection apparatus of claim 2, wherein the curving unit curves the sensor panel such that the radius of curvature of the sensor panel is variable.

4. The radiological image detection apparatus of claim 2, wherein the curving unit curves the sensor panel such that a direction of a straight line which connects a center of the sensor panel to the curvature center is variable.

5. The radiological image detection apparatus of claim 2, wherein the curving unit includes at least one driven member which is curved by physical stimulation and affixed to the sensor panel.

6. The radiological image detection apparatus of claim 5, wherein the driven member is a bimetal.

7. The radiological image detection apparatus of claim 6, wherein the curving unit has a driving unit configured to apply an electric current to the bimetal.

8. The radiological image detection apparatus of claim 5, wherein the curving unit has a plurality of the driven members, and applies the physical stimulation to the driven members independently of each other.

9. The radiological image detection apparatus of claim 5, wherein the curving unit has a support configured to support the sensor panel, the support includes a cover part configured to cover a surface opposite to a surface of the sensor panel which is in close cotact with the phosphor, and an engaging part configured to engage an edge of the sensor panel, and the driven member is provided on the cover part.

10. The radiological image detection apparatus of claim 9, wherein the support has flexibility.

11. The radiological image detection apparatus of claim 2, wherein the curving unit includes at least one driven member which is extended and retracted by physical stimulation, and has one end connected to the sensor panel, and another end which is fixed.

12. The radiological image detection apparatus of claim 1, wherein the phosphor further includes a non-columnar section that has a low porosity as compared to the columnar section, and the non-columnar section is in close contact with the sensor panel.

13. A radiation imaging apparatus comprising:

the radiological image detection apparatus of claim 2;

a radiation source configured to irradiate radiation toward the radiological image detection apparatus; and a detection unit configured to detect a relative position of the radiation source with respect to the radiological image detection apparatus, wherein the curving unit curves the sensor panel such that a position of the curvature center of the sensor panel is variable in accordance with the relative position of the radiation source which is detected by the detection unit.

14. The radiological image detection apparatus of claim 12, wherein the non-columnar section has a thickness ranging from 5 μm to 50 μm.

15. A radiation imaging apparatus comprising:

the radiological image detection apparatus of claim 1; and a radiation source configured to irradiate radiation toward the radiological image detection apparatus, wherein the curvature center of the sensor panel corresponds to a focal point of the radiation source.

16. The radiological image detection apparatus of claim 1, wherein the respective columnar crystals exist independently of each other with gaps around the columnar crystals.

17. The radiological image detection apparatus of claim 1, wherein the columnar crystals are kept perpendicular to a surface of the sensor panel.

* * * * *